United States Patent
Whitehurst et al.

(10) Patent No.: US 7,477,944 B1
(45) Date of Patent: *Jan. 13, 2009

(54) SYSTEMS AND METHODS FOR MODULATION OF PANCREATIC ENDOCRINE SECRETION AND TREATMENT OF DIABETES

(75) Inventors: Todd K Whitehurst, Santa Clarita, CA (US); James P McGivern, Stevenson Ranch, CA (US)

(73) Assignee: Boston Scientific Neuromodulation, Valencia, CA (US)

( * ) Notice: Subject to any disclaimer, the term of this patent is extended or adjusted under 35 U.S.C. 154(b) by 588 days.

This patent is subject to a terminal disclaimer.

(21) Appl. No.: 11/007,906

(22) Filed: Dec. 9, 2004

Related U.S. Application Data

(63) Continuation of application No. 09/993,084, filed on Nov. 6, 2001, now Pat. No. 6,832,114.

(60) Provisional application No. 60/252,626, filed on Nov. 21, 2000.

(51) Int. Cl.
*A61N 1/00* (2006.01)

(52) U.S. Cl. .................................................. 607/40

(58) Field of Classification Search ............. 607/40, 607/133; 600/300, 301, 554; 128/897–899, 128/920; 604/890.1, 891.1, 65–67
See application file for complete search history.

(56) References Cited

U.S. PATENT DOCUMENTS

| | | | |
|---|---|---|---|
| 4,646,744 A | 3/1987 | Capel | |
| 5,188,104 A | 2/1993 | Wernicke et al. | |
| 5,193,539 A | 3/1993 | Schulman et al. | |
| 5,193,540 A | 3/1993 | Schulman et al. | |
| 5,231,988 A | 8/1993 | Wernicke et al. | |
| 5,263,480 A | 11/1993 | Wernicke et al. | |
| 5,312,439 A | 5/1994 | Loeb | |
| 5,324,316 A | 6/1994 | Schulman et al. | |
| 5,405,367 A | 4/1995 | Schulman et al. | |
| 5,487,739 A | 1/1996 | Aebischer et al. | |
| 5,496,369 A | 3/1996 | Howard, III | |
| 5,540,734 A | 7/1996 | Zabara | |
| 5,589,183 A | 12/1996 | Jannetta | |
| 5,597,797 A | 1/1997 | Clark | |

(Continued)

FOREIGN PATENT DOCUMENTS

WO    WO-92/13592 A1    8/1992

(Continued)

OTHER PUBLICATIONS

Ahren, et al., "The Mechanism of Vagal Nerve Stimulation of Glucagon and Insulin Secretion in the Dog", Endocrinology, vol. 118, No. 4, (Apr. 1986), pp. 1551-1557.

(Continued)

*Primary Examiner*—George Manuel
(74) *Attorney, Agent, or Firm*—AdvantEdge Law Group, LLC

(57) ABSTRACT

Systems and methods for introducing one or more stimulating drugs and/or applying electrical stimulation to the pancreas and/or nerve fibers innervating the pancreas to treat or prevent diabetes and/or to modulate pancreatic endocrine secretions uses at least one system control unit (SCU) producing electrical pulses delivered via electrodes and/or producing drug infusion pulses, wherein the stimulating drug(s) are delivered via one or more pumps and infusion outlets.

16 Claims, 9 Drawing Sheets

U.S. PATENT DOCUMENTS

| | | | |
|---|---|---|---|
| 5,697,975 | A | 12/1997 | Howard, III et al. |
| 5,741,211 | A | 4/1998 | Renirie et al. |
| 5,782,798 | A | 7/1998 | Rise |
| 5,843,093 | A | 12/1998 | Howard, III |
| 5,919,216 | A | 7/1999 | Houben et al. |
| 5,989,920 | A | 11/1999 | Gerald et al. |
| 6,016,449 | A | 1/2000 | Fischell et al. |
| 6,051,017 | A | 4/2000 | Loeb et al. |
| 6,093,167 | A | 7/2000 | Houben et al. |
| 6,129,685 | A | 10/2000 | Howard, III |
| 6,464,687 | B1 | 10/2002 | Ishikawa et al. |
| 6,558,345 | B1 | 5/2003 | Houben et al. |
| 6,612,983 | B1 * | 9/2003 | Marchal ..................... 600/300 |

FOREIGN PATENT DOCUMENTS

| | | |
|---|---|---|
| WO | WO-93/02743 A1 | 2/1993 |
| WO | WO-98/37926 A1 | 9/1998 |
| WO | WO-98/43700 A1 | 10/1998 |
| WO | WO-98/43701 A1 | 10/1998 |
| WO | WO-01/80450 A1 | 8/2001 |

OTHER PUBLICATIONS

Ahren, et al., "Sympathetic Nerve Stimulation Versus Pancreatic Norepinephrine Infusion in the Dog: 1. Effects on Basal Release of Insulin and Glucagon", Endocrinology, vol. 121, No. 1, (Jul. 1987), pp. 323-331.

Bereiter, et al., "CNS Modulation of Pancreatic Endocrine Function Multiple Modes of Expression", Diabetologia, Suppl. 20, (Mar. 1981), pp. 417-425.

Berthoud, et al., "Characteristics of Gastric and Pancreatic Responses to Vagal Stimulation with Varied Frequencies: Evidence for Different Fiber Calibers?", Journal of the Autonomic Nervous System, vol. 19, No. 1, (Apr. 1987), pp. 77-84.

Berthoud, et al., "Localization of Vagal Preganglionics that Stimulate Insulin and Glucagon Secretion", AM J Physiol, vol. 258, No. 1 Part 2, (Jan. 1990), pp. R160-R168.

Bluher, et al. "Improvement of Insulin Sensitivity After Adrenalectomy in Patients with Pheochromocytoma", Diabetes Care, vol. 23, No. 10, (Oct. 1, 2000), pp. 1591-1592.

Brobeck, Jr., "Mechanism of Development of Obesity in Animals with Hypothalamic Lesions", Physiol Rev, vol. 26, (1946), pp. 541-559.

Broglio, et al., "Ghrelin, a Natural GH Secretagogue Produced by the Stomach, Induces Hyperglycemia and Reduces Insulin Secretion in Humans", The Journal of Clinical Endocrinology & Metabolism, vol. 86, No. 10, (Oct. 2001), pp. 5083-5086.

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781-790.

Davalli, et al., "Abnormal Sensitivity to Glucose of Human Islets Cultured in a High Glucose Medium: Partial Reversibility After an Additional Culture in a Normal Glucose Medium", Journal of Clinical Endocrinology and Metabolism, vol. 72, (1991), pp. 202-208.

DeNicola, et al., "Abnormal Regulation of Adrenal Function in Rats with Streptozotocin Diabetes", Horm Metab Res, vol. 9, (1977), pp. 469-473.

Dhillo, et al., "Hypothalami Peptides as Drug Targets for Obesity", Current Opinion in Pharmacology, vol. 1, No. 6, (2001), pp. 651-655.

Frankish, et al., "Neuropeptide Y, the Hypothalamus, and Diabetes: Insights into the Central Control of Metabolism", Peptides, vol. 16, No. 4, (1995), pp. 757-771.

Gardemann, et al., "Reinnervation of Pancreatic Islets and Regulation of Insulin Secretion by Hepatic Sympathetic Nerves After Intrportal Transplantation of Islets Into Livers of Diabetic Rats", Experimental and Clinical Endocrinology and Diabetes, vol. 103, Suppl. 2, (1995), pp. 107-111.

Holst, et al., "Nervous Control of Pancreatic Endocrine Secretion in Pigs. I. Insulin and Glucagon Responses to Electrical Stimulation of the Vagus Nerves", Acta Physiol Scand, vol. 111, No. 1, (Jan. 1981), pp. 1-7.

Hyde, et al., "Effects of Area Postrema Caudal Medial Nucleus of Solitary Tract Lesions on Food Intake and Body Weight", AM J Physiol, vol. 244, (1983), pp. R577-R587.

Ionescu, et al., "Increases in Plasma Insulin Levels in Response to Electrical Stimulation of the Dorsal Motor Nucleus of the Vagus Nerve", Endocrinology, vol. 112, No. 3, (Mar. 1983), pp. 904-910.

Jonkers, et al., "Influence of Cell Number on the Characteristics and Synchrony of Ca2+ Oscillations in Clusters on Mouse Pancreatic Islet Cells", Journal of Physiology, vol. 520, Part 3, (Nov. 1999), pp. 839-849.

Kakizaki, et al., "Neural Regulation of Auto-Grafted Islets of Langerhans", Nippon Geka Gakkai Zasshi, vol. 89, No. 3, (Mar. 1988), pp. 394-397.

Kakizaki, et al., "Neural Regulation of Heterotopic Islets of Langerhans", Surgery, vol. 100, No. 6, (Dec. 1986), pp. 997-1002.

Kurose, et al., "Glucagon, Insulin and Somatostatin Secretion in Response to Sympathetic Neural Activation in Streptozotocin0Induced Diabetic Rats. A study with the Isolated Perfused Rat Pancreas in Vitro", Diabetologia, vol. 35, No. 11, (Nov. 1992), pp. 1035-1041.

Kurose, et al., "Mechanism of Sympathetic Neural Regulation of Insulin, Somatostatin, and Glucagon Secretion", Am J Physiol, vol. 258, No. 1 part 1, (Jan. 1990), pp. E220-E227.

Lorrain, et al., "Adrenergic and Nonadrenergic Contransmitters Inhibit Insulin, Secretion During Sympathetic Stimulation in Dogs", AM J Physiol, vol. 263, No. 1 Part 1, (Jul. 1992), pp. E72-E78.

Mayfield, et al., "A Role for the Agouti-Related Protein Promoter in Obesity and Type 2 Diabetes", Biochemical and Biophysical Research Communications, vol. 287, No. 2, (Sep. 21, 2001), pp. 568-573.

Minami, et al., "Electrophysiological Properties and Glucose Responsiveness of Guinea-Pig Ventromedial Hypothalamic Neurons in Vitro", J Physiol, vol. 380, (1986), pp. 127-143.

Misler, et al., "Electrophysiology of Stimulus-Secretion Coupling In Human Beta-Cells", Diabetes, vol. 41, No. 10, (Oct. 1992), pp. 1221-1228.

Mondal, et al., "Orexins (hypocretins): Novel Hypothalami Peptides with Divergent Functions", Biochem Cell Biol, vol. 78, (2000), pp. 299-305.

Nakazato, et al., "A Role for Ghrelin In the Central Regulation of Feeding", Nature, vol. 409, No. 6817, (Jan. 11, 2001), pp. 194-198.

Nishi, et al., "Vagal Regulation of Insulin, Glucagon, and Somatostatin Secretion in Vitro in the Rat", J Clin Invest. vol. 79, No. 4, (Apr. 1987), pp. 1191-1196.

Oomura, et al., "Glucose and Osmosensitive Neurons of the Rat Hypothalamus", Nature, vol. 222, (1969), pp. 282-284.

Perkins, et al., "Activation of Brown Adipose Tissue Thermogenesis by the Ventromedial Hypothalamus", Nature, vol. 289, (Jan. 1981), pp. 401-402.

Pierroz, et al., "Chronic Administration of Neuropeptide Y Into the Lateral Ventricle Inhibits Both the Pituitary-Testicular Axis and Growth Hormone and Insulin-Like Growth Factor I Secretion in Intact Adult Male Rats", Endocrinology, vol. 137 No. 1, (Jan. 1996), pp. 3-12.

Pi-Sunyer, "Pathogenesis of Obesity", Drug Benefit Trands, vol. 12, Supp A, (2002), pp. 28-33.

Qu, et al., "Agouti-Related Protein is a Mediator of Diabetic Hyperphagia", Regulatory peptides, vol. 98, No. 1-2, (Apr. 2, 2001), pp. 69-75.

Ratner, "Innovations in Managing Type 2 Diabetes", Drug Benefit Trends, vol. 12, Supp A, (2000), pp. 34-43.

Ravier, et al., "Oscillations of Insulin Secretion Can be Triggered by Imposed Oscillations of Cytoplasmic Ca2+ or Metabolism in Normal Mouse Islets", Diabetes, vol. 48, No. 12, (Dec. 1999), pp. 2374-2382.

Sahu, et al., "Evidence that Neurotension Mediates the Central Effect of Leptin on Food Intake in Rat", Brain Research, vol. 888, No. 2, (Jan. 12, 2001), pp. 343-347.

Sawchenko, et al., "The Distribution of Cells of Organ of Serotonin Input to the Paraventricular and Supraoptic Nuclei of the Rat", Brain Reseach, vol. 277, (1983) pp. 355-360.

Shor-Posner, et al., "Deficits in the Control of Food Intake After Paraventricular Nucleus Lesions", Physiology and Behavior, vol. 35, (1985), pp. 883-890.

Tanaka, et al., "Effects of Intraventricular Administration of Neuropeptide Y on Feeding Behavior in Faster Female Rats with Ventromedial Hypothalamic Lesions", Regulatory Peptides, vol. 52, No. 1, (Jun. 16, 1994), pp. 47-52.

Thomas, et al., "Reversal of Type II (NIDDM) Diabetes by Pancreas Islet Transplantation: an Emerging New Concept in Pathophysiology of an Enigmatic Disease", Transplantation Proceedings, vol. 27, No. 6, (Dec. 1995), pp. 3167-3169.

Zaborszky, et al., "Brainstem Projection to the Hypothalamic Paraventricular Nucleus in the Rat, a CCK-Containing Long Ascending Pathway", Brain Research, vol. 303, (1984), pp. 225-231.

"Hormones Found in the Brain May Determine How Much You Eat and Affect Obesity and Diabetes", printed Dec. 12, 2002, pp. 1-2.

"Neurogen Commences Phase Ib Human Clinical Trials with Anti-Obesity Drug", printed Dec. 6, 2002, p. 1.

"Obesity: Mechanism Neuropeptide Y Receptor Antagonists", Neurogen Corporation, printed Aug. 21, 2002, pp. 1-2.

Wahlestedt, et al. "Neuropeptide Y and Related Peptides", printed Jul. 10, 2001, pp. 1-10.

Wells, William A., "Possible Finding on Weight Control", Standford online Report, printed Dec. 9, 2002, pp. 1-3.

Clore Laboratory: News Diabetes, Obesity and Metabolic Research, "Jun. 7, 2001—Hot topic poster European Obesity Congress", printed Dec. 12, 2002, p. 1.

Whitehurst inventor for; U.S. Appl. No. 09/993,086, filed Nov. 6, 2001; entitled "Systems and Methods for Treatment of Obesity and Eating Disorders by Electrical Brain Stimulation and/or Drug Infusion".

Whitehurst inventor for; U.S. Appl. No. 09/993,085; filed Nov. 6, 2001; entitled "Systems and Methods for Treatment of Diabetes by Electrical Brain Stimulation and/or Drug Infusion".

* cited by examiner

SYSTEMS AND METHODS FOR MODULATION OF PANCREATIC ENDOCRINE SECRETION AND TREATMENT OF DIABETES

The present application is a continuation of U.S. patent application Ser. No. 09/993,084, filed Nov. 6, 2001, to be issued as U.S. Pat. No. 6,832,114, on Dec. 14, 2004, which application claims the benefit of U.S. Provisional Patent Application Ser. No. 60/252,626, filed Nov. 21, 2000, which provisional application and soon to issue patent are incorporated herein by reference.

FIELD OF THE INVENTION

The present invention generally relates to drug delivery and electrical stimulation systems and methods, and more particularly relates to utilizing one or more devices to deliver electrical stimulation and/or one or more stimulating drugs for the modulation of pancreatic endocrine secretion and as a treatment for diabetes.

BACKGROUND OF THE INVENTION

Twelve to fifteen million people in the United States suffer from diabetes mellitus (which is often, as herein, simply referred to as diabetes). Diabetes is a syndrome characterized by disordered metabolism and inappropriately high levels of blood glucose, i.e., hyperglycemia. Diabetes is classified into two distinct types. Type 1, also known as Insulin-Dependent Diabetes Mellitus (IDDM), is believed to be due to autoimmune destruction of beta cells in the pancreas, which are the only cells in the body that produce and secrete insulin. Type 1 occurs most commonly in juveniles but occasionally in adults. Type 2, also known as Non-Insulin-Dependent Diabetes Mellitus (NIDDM), is a milder form of diabetes that usually occurs in adults.

Up to about 10% of people with diabetes have type 1 diabetes, and are dependent on daily exogenous insulin. Insulin, a small protein, is degraded when taken orally; thus, it must be administered parenterally. Thus, most patients take insulin through injection. An increasing number are receiving insulin through a percutaneous pump, but this requires external apparatus that must be worn continuously. A fully implantable pump is also available, requiring monthly visits to a physician to refill the pump. An inhaled version of insulin is under development. Additional treatment options are needed.

SUMMARY OF THE INVENTION

The invention disclosed and claimed herein provides modulation of pancreatic endocrine secretion and treatment or prevention of diabetes, via one or a combination of systems and methods. Some systems and methods of the present invention provide electrical stimulation of pancreatic cells, and particularly of alpha and delta cells, as well as beta cells. Stimulation to depolarize/hyperpolarize alpha and delta cells modulates the secretion of glucagon and somatostatin, respectively, which in turn affects the secretion of insulin by beta cells. In addition, the present invention teaches hyperpolarization of pancreatic beta cells, for inhibiting the secretion of insulin during periods of hypoglycemia. Further, the present invention teaches effective frequencies for electrical stimulation, so that stimulation of pancreatic islet cells is maximized while the stimulation of other structures is minimized.

Additional systems and methods taught herein provide electrical stimulation of autonomic nerves and/or ganglia innervating the pancreas, thereby modulating insulin and glucagon secretion. For example, stimulation to decrease the excitement of sympathetic input to the pancreatic beta cells will increase insulin production.

Other systems and methods of the present invention provide the application of a stimulating drug(s) alone or in combination with electrical stimulation. These drugs may modulate the release of insulin, somatostatin, and glucagon. This invention also includes the possibility of combining stimulation with medication released from an implanted reservoir (i.e., a drug pump).

Electrical and/or drug stimulation of specific sites innervating and/or within the pancreas, and the resulting changes in secretion of insulin, glucagon, and somatostatin, may have significant therapeutic benefit in the control of diabetes. In addition, it is believed that 1) insulin and somatostatin secretions induced by glucose are inhibited during SNS through alpha-adrenergic activation, 2) insulin and somatostatin secretions are stimulated during SNS through beta-adrenergic activation, and 3) SNS-induced glucagon secretion occurs mainly through alpha-adrenergic activation.

This invention may prove beneficial in cases of transplanted beta cells, wherein the cells have no innervation to modulate insulin secretion. This invention may also prove beneficial in cases of blunted or absent response of endogenous pancreatic endocrine tissue to neural stimulation. Additional potential (but not necessary) uses of the present invention include, but are not limited to, application to diabetes prevention, e.g., by inhibiting glucagon and/or somatostatin from attenuating the effects of insulin, possibly by decreasing glucagon and/or somatostatin plasma levels.

The invention is carried out via one or more system control units (SCUs) that apply electrical stimulation and/or one or more stimulating drugs to one or more predetermined stimulation sites. In some forms of SCUs, one or more electrodes are surgically implanted to provide electrical stimulation from an implantable signal/pulse generator (IPG) and/or one or more infusion outlets and/or catheters are surgically implanted to infuse drug(s) from an implantable pump. When necessary and/or desired, an SCU provides both electrical stimulation and one or more stimulating drugs. In other forms of an SCU, a miniature implantable neurostimulator (a.k.a., a microstimulator), such as a Bionic Neuron (also referred to as a BION® microstimulator), is implanted. Some forms of the disclosed systems also include one or more sensors for sensing symptoms or other conditions that may indicate a needed treatment.

The SCU may include a programmable memory for storing data and/or control parameters. This allows stimulation and control parameters to be adjusted to levels that are safe and efficacious with minimal discomfort. Electrical and drug stimulation may be controlled independently; alternatively, electrical and drug stimulation may be coupled, e.g., electrical stimulation may be programmed to occur only during drug infusion.

According to some embodiments of the invention, the electrodes used for electrical stimulation are arranged as an array on a thin implantable lead. The SCU may be programmed to produce either monopolar electrical stimulation, e.g., using the SCU case as an indifferent electrode, or bipolar electrical stimulation, e.g., using one of the electrodes of the electrode array as an indifferent electrode. The SCU may include a means of stimulating tissue or infusing a stimulating drug(s) either intermittently or continuously. Specific stimulation/ infusion parameters may provide therapy for, e.g., varying types and degrees of severity of diabetes.

The SCU used with the present invention possesses one or more of the following properties, among other properties:
- at least two electrodes for applying stimulating current to surrounding tissue and/or a pump and at least one outlet for delivering a drug or drugs to surrounding tissue;
- electronic and/or mechanical components encapsulated in a hermetic package made from biocompatible material(s);
- an electrical coil inside the package that receives power and/or data by inductive or radio-frequency (RF) coupling to a transmitting coil placed outside the body, avoiding the need for electrical leads to connect devices to a central implanted or external controller;
- means for receiving and/or transmitting signals via telemetry;
- means for receiving and/or storing electrical power within the SCU; and
- a form factor making the SCU implantable in a target area in the body.

The power source of the SCU is realized using one or more of the following options, or the like:
(1) an external power source coupled to the SCU via a radio-frequency (RF) link;
(2) a self-contained power source made using any means of generation or storage of energy, e.g., a primary battery, a replenishable or rechargeable battery, a capacitor, a supercapacitor; and/or
(3) if the self-contained power source is replenishable or rechargeable, a means of replenishing or recharging the power source, e.g., an RF link, an optical link, or other energy-coupling link.

According to certain embodiments of the invention, an SCU operates independently. According to various embodiments of the invention, an SCU operates in a coordinated manner with other implanted SCUs, other implanted devices, or with devices external to the patient's body.

According to several embodiments of the invention, an SCU incorporates means of sensing the disorder or symptoms thereof, or other measures of the state of the patient. Sensed information may be used to control the electrical and/or drug stimulation parameters of the SCU in a closed loop manner. According to some embodiments of the invention, the sensing and stimulating means are incorporated into a single SCU. According to several embodiments of the invention, the sensing means communicates sensed information to at least one SCU with stimulating means.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1:
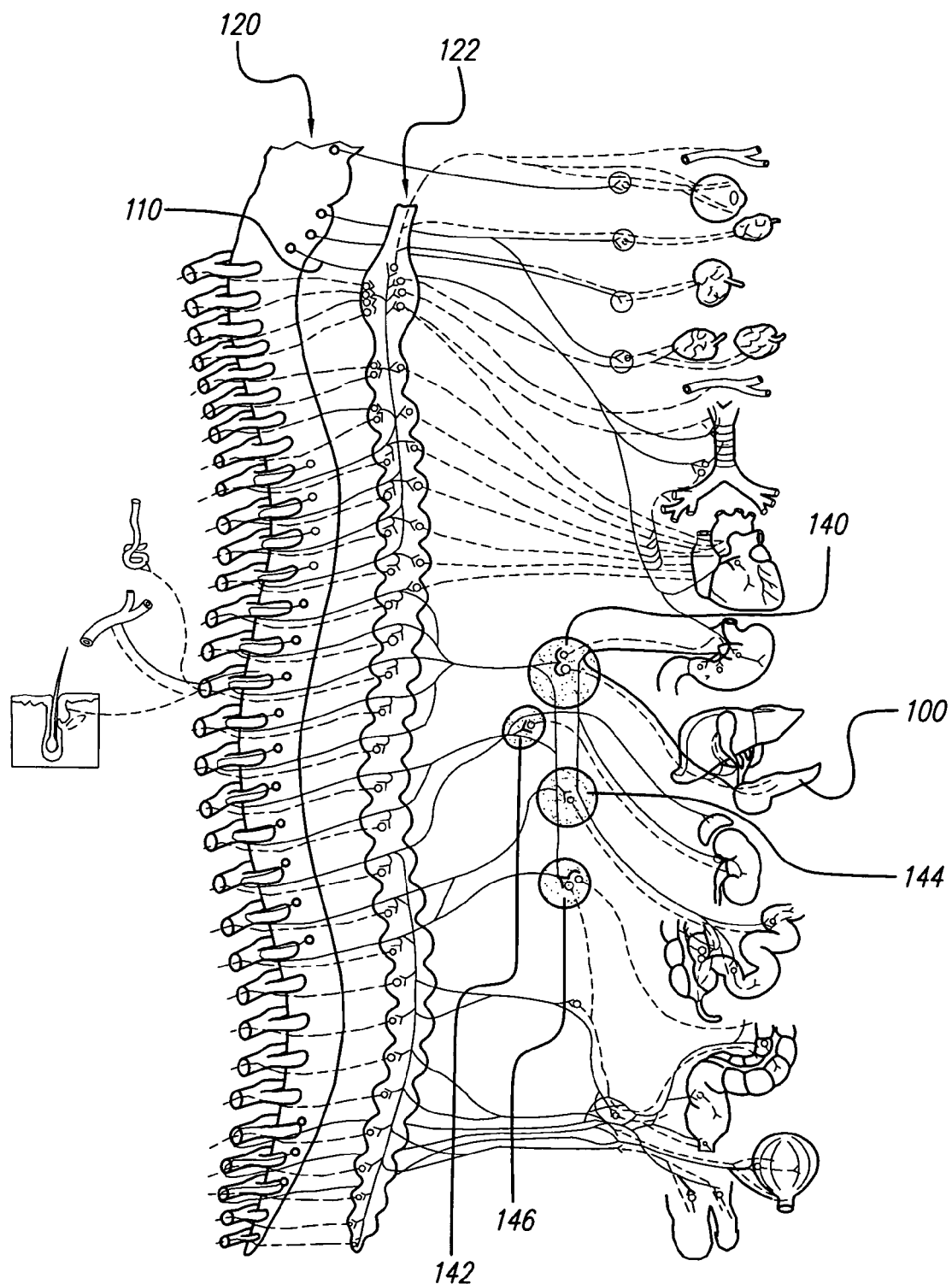
FIG. 1 is a schematic of the autonomic nervous system.

The following description is of the best mode presently contemplated for carrying out the invention. This description is not to be taken in a limiting sense, but is made merely for the purpose of describing the general principles of the invention. The scope of the invention should be determined with reference to the claims.

Insulin is released only by beta cells in pancreatic islets (i.e., small isolated masses of one type of tissue within a different type), known as the islets of Langerhans. Insulin is one of the endocrine system secretions (i.e., secretions that are distributed in the body by way of the bloodstream) of the islets of Langerhans, which help integrate and control bodily metabolic activity. The islets also include alpha cells, which produce glucagon, delta cells, which produce somatostatin, and a small number of PP cells, which produce pancreatic polypeptide. The beta cells tend to be in the center of the pancreatic islets, while the alpha cells tend to occupy the periphery. The beta cells generally constitute 60-70% of the islets, the alpha cells 20-25%, and the delta cells approximately 10%. Gap junctions exist between neighboring islet cells, permitting the ready flow of molecules and electrical currents between cells. If these gap junctions are disrupted, insulin secretion is markedly reduced. Islet cell clusters function better as electrical than biochemical syncytia.

Under normal circumstances, insulin is secreted by the beta cells in response to an elevated level of plasma glucose via the following steps. The transportation of glucose across the beta cell membrane is facilitated by a specific transporter molecule known as GLUT-2. Once inside the beta cell, the enzyme glucokinase causes glucose to phosphorylate (i.e., to take-up or combine with phosphoric acid or a phosphorus-containing group), which prevents its efflux. High levels of glucose and glucose-6-phosphate within the cell lead to a rapid increase in the ratio of adenosine triphosphate (ATP) to adenosine diphosphate (ADP), which leads directly to the closure of ATP-sensitive transmembrane potassium ion (K+) channels. This prevents the normal efflux of K+ from the beta cell, and the cell depolarizes. Voltage-regulated calcium ion (Ca++) channels open in response to this depolarization, allowing an influx of Ca++. Elevated intracellular Ca++ leads to activation of protein kinases and ultimately to fusion of insulin-containing secretory granules with the beta cell membrane, thus leading to exocytosis of insulin into the systemic circulation. This entire sequence occurs within one minute of exposure to elevated glucose levels.

Insulin is a hormone that serves a variety of functions. Its primary action is to potentiate the uptake of glucose from the bloodstream by muscle and adipose tissue. It also promotes conversion of glucose to a storage form (i.e., glycogen) in the liver and to fat in adipose tissue. These actions serve to decrease the circulating level of glucose.

Glucagon is released primarily under conditions of hypoglycemia, and it tends to have effects opposite those of insulin. Release of glucagon is also promoted by alpha-adrenergic neurotransmitters, and it is inhibited by beta-adrenergic neurotransmitters, cholinergic neurotransmitters, and insulin.

Somatostatin secretion is stimulated by glucose, glucagon, beta-adrenergic neurotransmitters, cholinergic neurotransmitters, and a number of other chemical factors; its release is inhibited by insulin and by alpha-adrenergic neurotransmitters. Somatostatin tends to inhibit the release of both insulin and glucagon.

Secretion of insulin may also be modulated by other neural and chemical factors. Parasympathetic stimulation and the consequent release of acetylcholine tends to increase the secretion of insulin. Sympathetic stimulation produces competing effects, as beta-adrenergic neurotransmitters tend to increase insulin secretion while alpha-adrenergic neurotransmitters tend to decrease insulin secretion. Insulin secretion is also increased by a number of other factors, including K+, Ca++, arginine, lysine, glucagon, glucagon-like peptide 1, gastric inhibitory peptide (GIP), secretin, cholecystokinin (CCK), and beta-3-agonists. Insulin secretion is also decreased by a number of other factors, including somatostatin, galanin, pancreastatin, and leptin.

Parasympathetic Stimulation

A significant body of research exists describing the influence of parasympathetic activity on insulin secretion by the pancreatic beta cells. Parasympathetic nerve stimulation in the dog produces a marked increase in insulin secretion and a moderate increase in glucagon secretion. In addition, parasympathetic activation produces increased insulin and glucagon secretion in proportion to pulse frequency, while inhibiting somatostatin release. Cholinergic neurotransmitters, which are the neurotransmitters most commonly secreted by parasympathetic nerve fibers, were found to be responsible for this influence. However, findings also suggest that a non-cholinergic neurotransmitter(s) may also be involved in parasympathetic regulation of pancreatic hormone secretion.

The dependence of insulin and glucagon secretion on parasympathetic nerve stimulation parameters was quantified in 1981 by Holst, et al., in a study on young pigs. [Hoist, et al. "Nervous control of pancreatic endocrine secretion in pigs." Acta. Physiol. Scand.; 1981 January; 111(1):1-7.] The responses depended on the frequency of the stimulation. The threshold frequency was less than 1 Hz and the maximum response was reached at 8-12 Hz. Further, with maximal stimulation, the quantity of insulin secreted was comparable to the amount released during glucose stimulation.

However, both the insulin and the glucagon response were critically dependent on the blood glucose concentration during the stimulation. The glucagon response was inversely correlated to blood glucose, whereas the insulin response was positively correlated to blood glucose at concentrations above 4.5 mmol/L. Below this glucose concentration, there was no detectable insulin response to parasympathetic nerve stimulation, and above 8.0 mmol/L there was no glucagon response to parasympathetic nerve stimulation. Secretion of glucagon and insulin was maintained for up to 30 minutes of stimulation.

In 1987, Berthoud demonstrated that the response of abdominal and thoracic organs to parasympathetic nerve activity depends on the frequency of electrical stimulation of the nerve. [Berthoud, et al. "Characteristics of gastric and pancreatic responses to vagal stimulation with varied frequencies: evidence for different fiber calibers?" Journ. Auton. Nerv. Syst.; 1987 April; 19(1):77-84.] The frequency-response curves show distinctly different profiles for the gastric, pancreatic, and cardiovascular responses: acid secretion was near maximal at less than 1 Hz, insulin and glucagon responses were near maximal at approximately 3 Hz, and cardiovascular responses were near maximal at approximately 15 Hz. These results suggest that the gastric parietal cells may be innervated by small C-fiber caliber axons, and the pancreatic islets, by axons in the large C-fiber or small B-fiber range. Alternatively, these findings could reflect differences in neuron and end organ coupling. These findings also suggest the feasibility of frequency selection to maximize parasympathetically mediated responses while minimizing any secondary responses.

The specific parasympathetic pathways innervating the pancreatic islets are known. Three branches of the vagus nerve mediate both insulin and glucagon release: the posterior gastric branch (198% and 117% increase from basal for insulin and glucagon, respectively), the anterior gastric branch (177% insulin increase and 104% glucagon increase), and the hepatic branch (103% insulin increase and 60% glucagon increase). In contrast, unreliable and insignificant hormonal responses were produced by the electrical stimulation of fibers projecting from two other branches of the vagus nerve: the posterior celiac branch (12% insulin increase and 12% glucagon increase) and the accessory celiac branch (15% insulin increase and 31% glucagon increase).

Sympathetic Stimulation

The sympathetic nervous system also exerts a significant influence on insulin and glucagon secretion by the pancreatic islets. The sympathetic splanchnic nerve, arising from the paraspinal sympathetic trunks, is the primary sympathetic influence on the pancreas. Its primary neurotransmitter is norepinephrine, which activates alpha-adrenergic and beta-1-adrenergic receptors, but has relatively little influence on beta-2-adrenergic receptors.

In 1990, Kurose thoroughly investigated the effects of electrical stimulation of the left splanchnic nerve on insulin, somatostatin, and glucagon secretion from the isolated, perfused rat pancreas. [Kurose, et al. "Mechanism of sympathetic neural regulation of insulin, somatostatin, and glucagon secretion." Am. Journ. Physiol.; 1990 January; 258(1 Pt 1):E220-7.] Splanchnic nerve stimulation (SNS) performed by square-wave impulses produced a 10-fold increase in norepinephrine. Both insulin and somatostatin output in the presence of 16.7 mM glucose were inhibited during SNS by 85% and 56% of the basal value, respectively. Glucagon output in the presence of 5.5 mM glucose was increased 20-fold by SNS.

Kurose, et al. further demonstrated that activation of different subtypes of sympathetic (adrenergic) receptors, specifically alpha-adrenergic and beta-adrenergic, produced significantly different results on insulin, glucagon, and somatostatin secretion. Propranolol, a nonselective beta-adrenoceptor antagonist, further decreased insulin and somatostatin output during SNS, while the glucagon response to SNS tended to be enhanced, although not significantly, by simultaneous infusion of propranolol.

In contrast, phentolamine, a nonselective alpha-adrenoceptor antagonist, attenuated the SNS-induced inhibition of insulin and somatostatin output by 50 and 40%, respectively. The SNS-induced glucagon increase was abolished by phentolamine alone or by phentolamine plus propranolol. With phentolamine plus propranolol, insulin and somatostatin output remained decreased after SNS.

In 1992, Kurose also found that, in diabetic rats, the sensitivity of alpha and delta cells to sympathetic neural activation is blunted, whereas the sensitivity of beta cells is enhanced. [Kurose, et al. "Glucagon, insulin and somatostatin secretion in response to sympathetic neural activation in streptozotocin-induced diabetic rats." Diabetologia; 1992 November; 35(11):1035-41.]

Later studies confirmed that inhibition of insulin secretion by the sympathetic nervous system may be mediated by norepinephrine acting on alpha-2-adrenoceptors and also by a nonadrenergic cotransmitter that maintains transmission despite norepinephrine deficiency. It was postulated that the nonadrenergic cotransmitter(s) act, at least partly, via the opening of ATP-modulated K+ channels. Its action may be antagonized by glibenclamide, and its release can be prevented by the neuronal blocking agent bretylium.

Beta Cell Transplantation

Since a common defect in all types of diabetes is a defect or a loss of pancreatic islet beta cells, transplantation of such cells has been explored as a possible therapy for diabetes. It has been demonstrated that grafted islets are not reinnervated, and thus are not under neural control. However, it was also demonstrated that these grafted islets release insulin in response to increased levels of glucose, and that at least one parasympathetic agonist, methacholine, causes the grafted islets to increase insulin secretion.

Stimulation Examples

Relatively low-frequency electrical stimulation (i.e., less than about 50-100 Hz) has been demonstrated to excite neural tissue, leading to increased neural activity. Similarly, excitatory neurotransmitters, agonists thereof, and agents that act to increase levels of an excitatory neurotransmitter(s) have been demonstrated to excite neural tissue, leading to increased neural activity. Inhibitory neurotransmitters have been demonstrated to inhibit neural tissue, leading to decreased neural activity; however, antagonists of inhibitory neurotransmitters and agents that act to decrease levels of an inhibitory neurotransmitter(s) have been demonstrated to excite neural tissue, leading to increased neural activity.

Relatively high-frequency electrical stimulation (i.e., greater than about 50-100 Hz) is believed to have an inhibitory effect on neural tissue, leading to decreased neural activity. Similarly, inhibitory neurotransmitters, agonists thereof, and agents that act to increase levels of an inhibitory neurotransmitter(s) have an inhibitory effect on neural tissue, leading to decreased neural activity. Excitatory neurotransmitters have been demonstrated to excite neural tissue, leading to increased neural activity; however, antagonists of excitatory neurotransmitters and agents that act to decrease levels of an excitatory neurotransmitter(s) inhibit neural tissue, leading to decreased neural activity.

Electrical stimulation has been proposed for treating diabetes. However, the electrical stimulation was applied either to pancreatic beta cells (U.S. Pat. Nos. 5,919,216 and 6,093,167) or to the vagus nerve (U.S. Pat. No. 5,231,988) to treat endocrine disorders. In addition, these devices require significant surgical procedures for placement of electrodes, catheters, leads, and/or processing units. These devices may also require an external apparatus that needs to be strapped or otherwise affixed to the skin.

Figure 2:
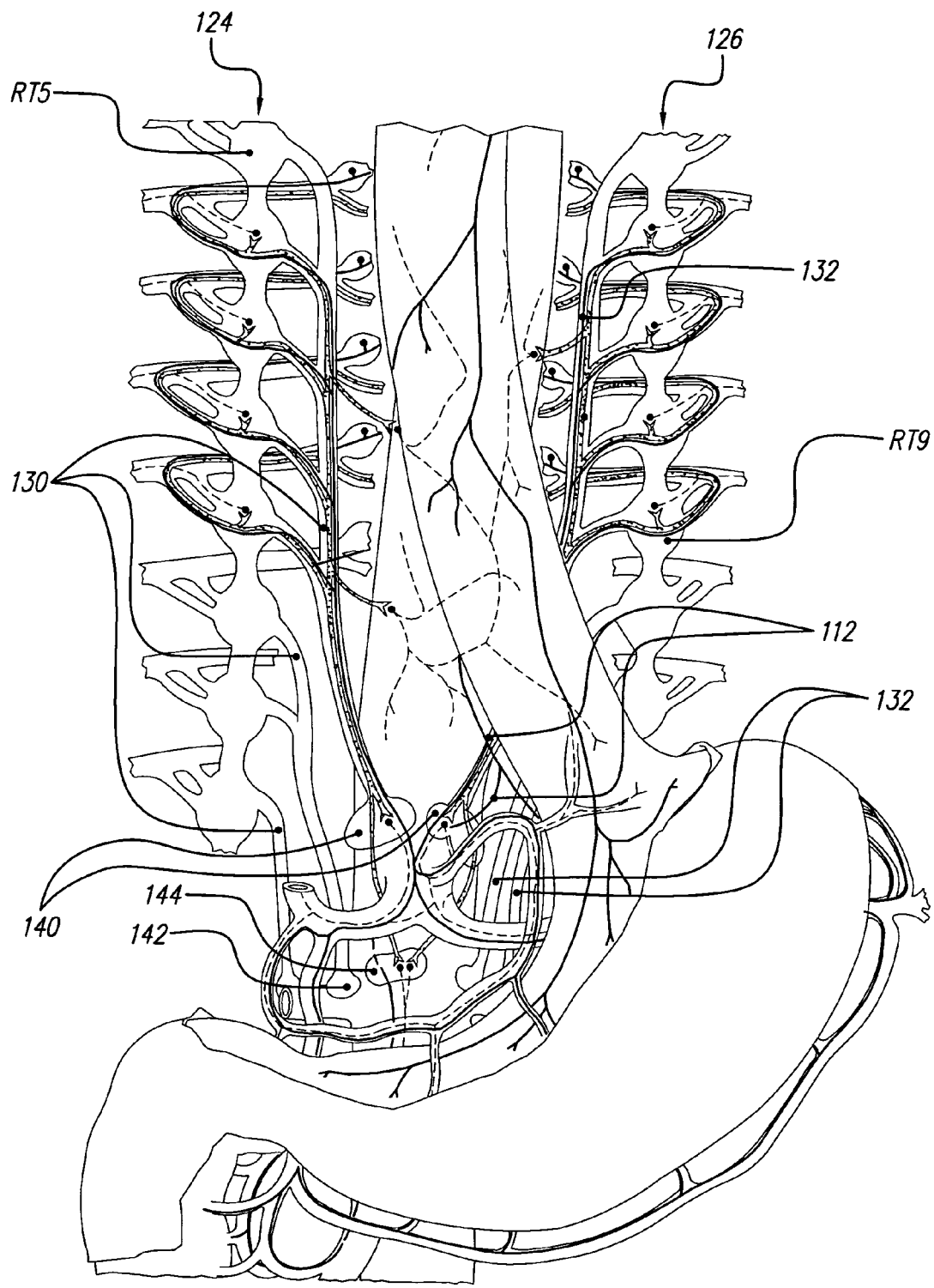
FIG. 2 depicts the innervation of areas and structures in the vicinity of the pancreas.
Figure 3A:
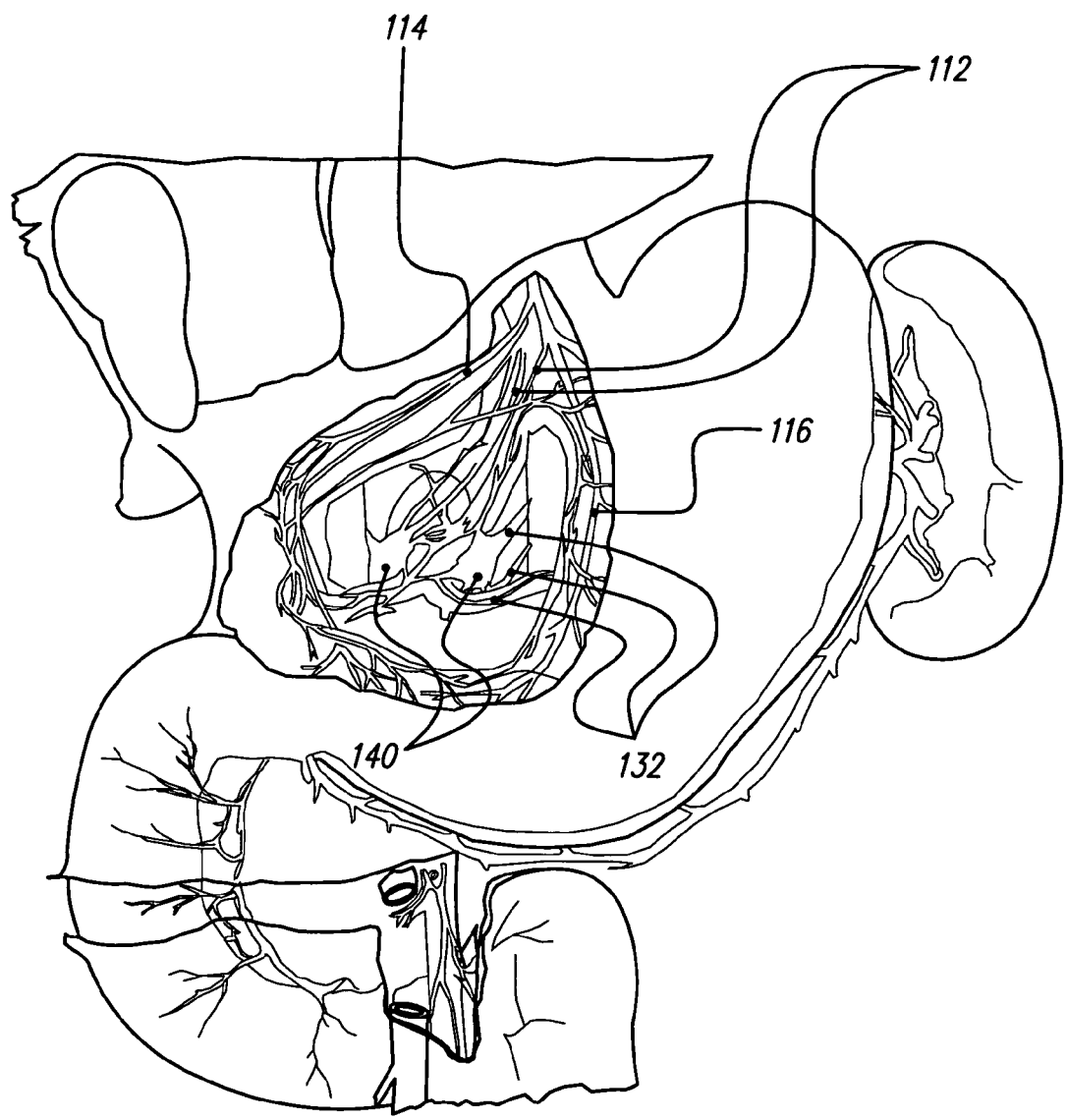
FIG. 3A shows some of the nerves in the vicinity of the pancreas.
Figure 3B:
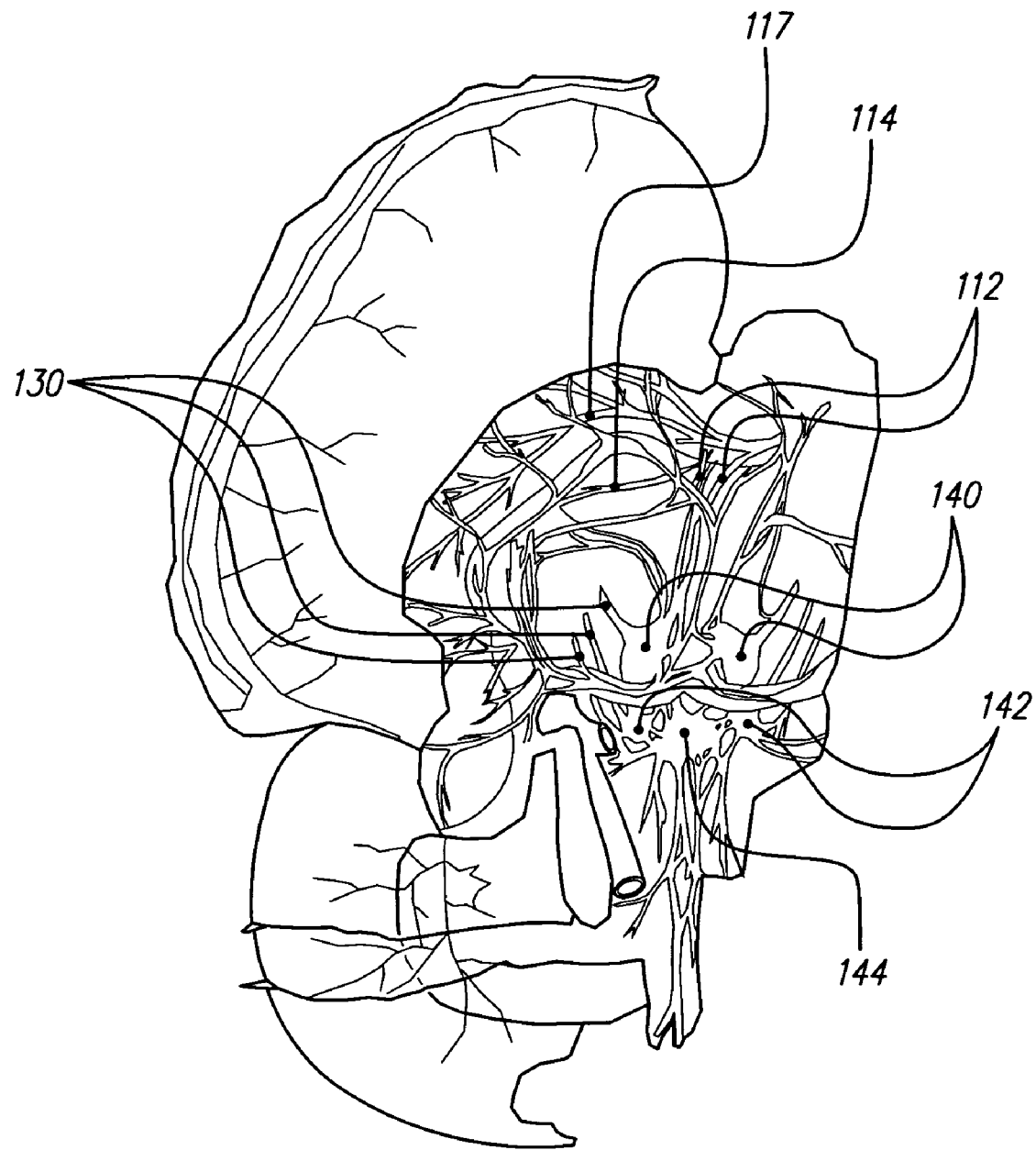
FIG. 3B is a view of some of the nerves in the vicinity of the pancreas, with the stomach reflected.
Figure 3C:
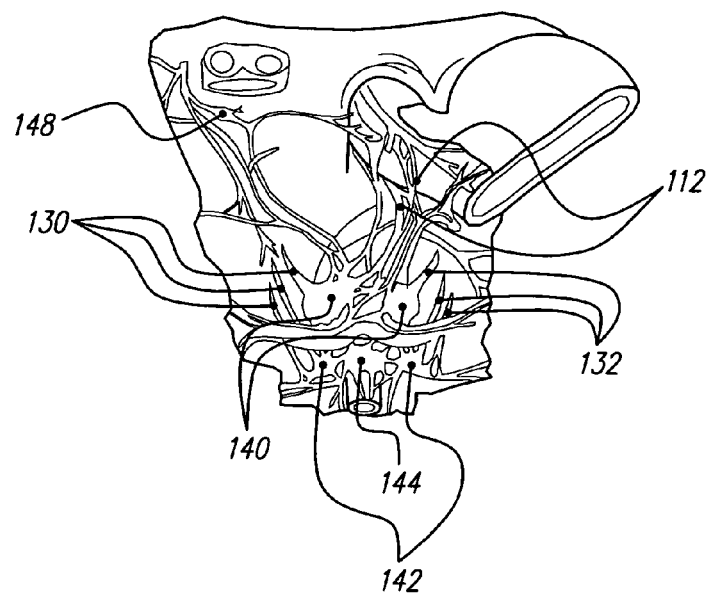
FIG. 3C is a view of some of the nerves in the vicinity of the pancreas, and more particularly, in the hiatal region.

FIG. 1 is a schematic of the autonomic nervous system, FIG. 2 depicts the innervation of areas and structures in the vicinity of the pancreas, and FIGS. 3A, 3B, and 3C are different views of nerves in the vicinity of the pancreas. The pancreas 100 receives parasympathetic input from various branches of the vagus nerve 110. These vagal nerve branches include the celiac branches 112, the anterior hepatic branch 114, the anterior gastric branch 116, and the posterior gastric branch 117.

Sympathetic input from the spinal cord 120 travels through right and left thoracic ganglia of the sympathetic trunks 122. These ganglia are designated, for example, RT5 for the right fifth thoracic ganglion of the right sympathetic trunk 124 and LT9 for the left ninth thoracic ganglion of the left sympathetic trunk 126. Signals are carried from the thoracic region of the sympathetic trunks by the right greater, lesser, and least splanchnic nerves 130 and the left greater, lesser, and least splanchnic nerves 132. Sympathetic signals travel through a number of ganglia: the celiac ganglia 140, the aorticorenal ganglia 142, the super mesenteric ganglion 144, the inferior mesenteric ganglion 146, and the phrenic ganglion 148.

The pancreas is comprised mostly of acini and islets of Langerhans. Acini comprise over 80% of the gland. Each acinus is lined with wedge-shaped acinar cells. Acinar cells are the site of production and secretion of the digestive enzymes.

Capillaries allow hormones from the islet cells to reach the acinar cells. Islets of Langerhans are scattered irregularly throughout the pancreas and contain the islet cells, which are responsible for secreting the endocrine hormones: insulin, glucagon, somatostatin, and pancreatic polypeptide. The insulin-secreting beta cells comprise about 60-70% of the islet. They are surrounded by a mantle of glucagon-secreting alpha cells, somatostatin-secreting delta cells, and pancreatic polypeptide-secreting PP cells. The various cells of the islets are separated from one another by a rich capillary network.

The present invention provides electrical and/or drug stimulation to at least one or more of the above mentioned areas as a treatment for diabetes. Herein, stimulating drugs comprise medications, anesthetic agents, synthetic or natural hormones, neurotransmitters, cytokines and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein may include stimulation of cell bodies and axons in the area.

In some alternatives, an implantable signal generator and electrode(s) and/or an implantable pump and catheter(s) are used to deliver electrical stimulation and/or one or more stimulating drugs to the target area(s). One or more electrodes are surgically implanted to provide electrical stimulation, and/or one or more catheters are surgically implanted to infuse the stimulating drug(s).

In some embodiments, electrical stimulation is provided by one or more system control units (SCUs) that are small, implantable stimulators, referred to herein as microstimulators. The microstimulators of the present invention may be similar to or of the type referred to as BION® devices (see FIGS. 4A, 4B, and 4C). The following documents describe various details associated with the manufacture, operation and use of BION implantable microstimulators, and are all incorporated herein by reference:

| Application/<br>Patent/<br>Publication No. | Filing/Publication<br>Date | Title |
|---|---|---|
| U.S. Pat.<br>No. 5,193,539 | Issued<br>Mar. 16, 1993 | Implantable Microstimulator |
| U.S. Pat.<br>No. 5,193,540 | Issued<br>Mar. 16, 1993 | Structure and Method of<br>Manufacture of an Implantable<br>Microstimulator |
| U.S. Pat.<br>No. 5,312,439 | Issued<br>May 17, 1994 | Implantable Device Having an<br>Electrolytic Storage Electrode |
| U.S. Pat.<br>No. 5,324,316 | Issued<br>Jun. 28, 1994 | Implantable Microstimulator |
| U.S. Pat.<br>No. 5,405,367 | Issued<br>Apr. 11, 1995 | Structure and Method of<br>Manufacture of an<br>Implantable Microstimulator |
| PCT Publication<br>WO 98/37926 | Published<br>Sep. 3, 1998 | Battery-Powered Patient<br>Implantable Device |
| PCT Publication<br>WO 98/43700 | Published<br>Oct. 8, 1998 | System of Implantable Devices For<br>Monitoring and/or Affecting Body<br>Parameters |
| PCT Publication<br>WO 98/43701 | Published<br>Oct. 8, 1998 | System of Implantable Devices For<br>Monitoring and/or Affecting Body<br>Parameters |
| U.S. Pat.<br>No. 6,051,017<br>(application Ser.<br>No. 09/077,662) | Issued<br>Apr. 18, 2000<br>(filed<br>May 29, 1998) | Improved Implantable<br>Microstimulator and Systems<br>Employing Same |
| | Published<br>September, 1997 | Micromodular Implants to Provide<br>Electrical Stimulation of Paralyzed<br>Muscles and Limbs, by Cameron,<br>et al., published in IEEE<br>Transactions on Biomedical<br>Engineering, Vol. 44, No. 9, pages<br>781-790. |

Figure 4A:
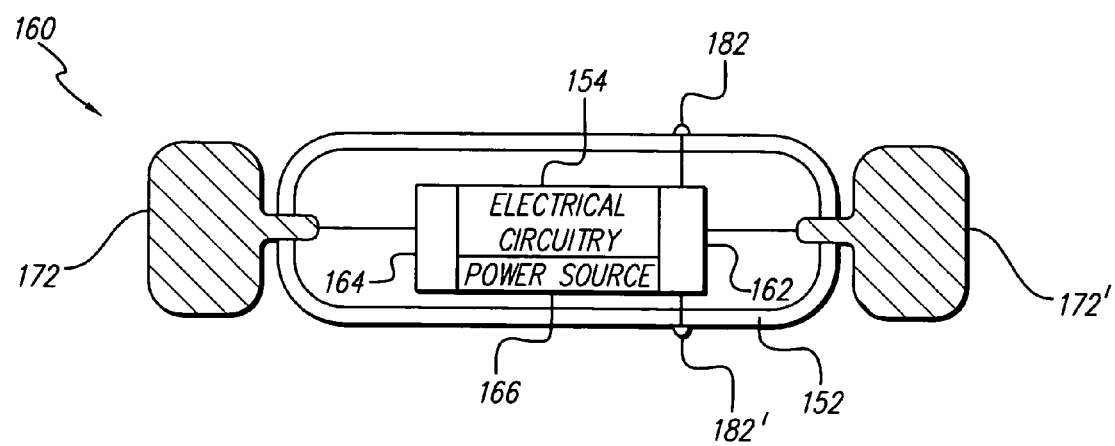
FIGS. 4A, 4B, and 4C show some possible configurations of an implantable microstimulator of the present invention.
Figure 4B:
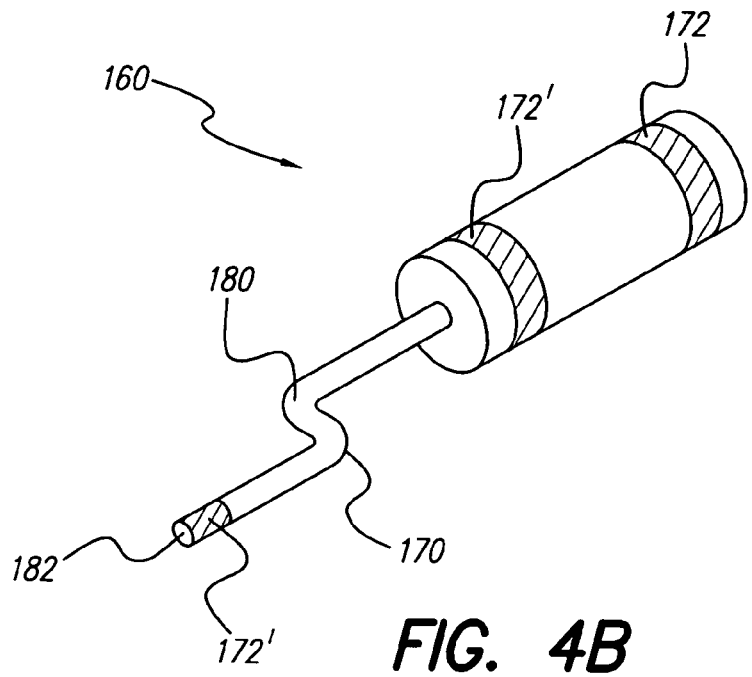
Figure 4C:
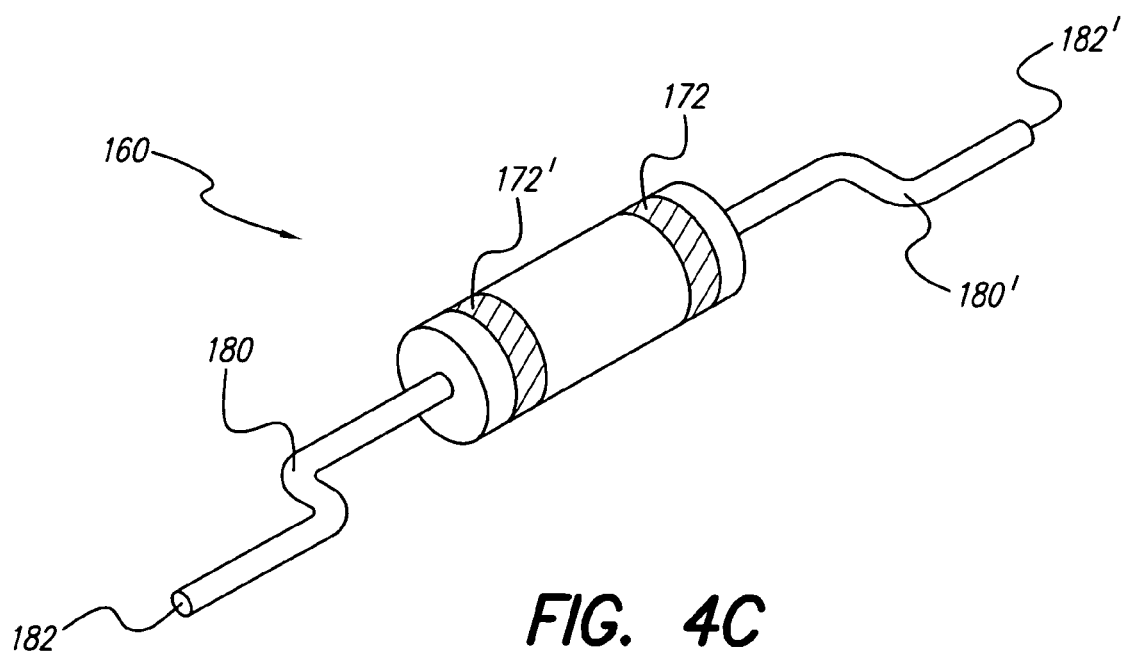

As shown in FIGS. 4A, 4B, and 4C, microstimulator SCUs 160 may include a narrow, elongated capsule 152 containing electronic circuitry 154 connected to electrodes 172 and 172', which may pass through the walls of the capsule at either end. Alternatively, electrodes 172 and/or 172' may be built into the case and/or arranged on a catheter 180 (FIG. 4B) or at the end of a lead, as described below. As detailed in the referenced patents, electrodes 172 and 172' generally comprise a stimulating electrode (to be placed close to the target tissue) and an indifferent electrode (for completing the circuit). Other configurations of microstimulator SCU 160 are possible, as is evident from the above-referenced patent publications, and as described in more detail herein.

Certain configurations of implantable microstimulator SCU 160 are sufficiently small to permit placement in or adjacent to the structures to be stimulated. For instance, in these configurations, capsule 152 may have a diameter of about 4-5 mm, or only about 3 mm, or even less than about 3 mm. In these configurations, capsule length may be about 25-35 mm, or only about 20-25 mm, or even less than about 20 mm. The shape of the microstimulator may be determined by the structure of the desired target, the surrounding area, and the method of implantation. A thin, elongated cylinder with electrodes at the ends, as shown in FIGS. 4A, 4B, and 4C, is one possible configuration, but other shapes, such as cylinders, disks, spheres, and helical structures, are possible, as are additional electrodes, infusion outlets, leads, and/or catheters.

Microstimulator SCU 160, when certain configurations are used, may be implanted with a surgical insertion tool such as the tool specifically designed for the purpose, or may be injected (e.g., via a hypodermic needle). Alternatively, microstimulator SCU 160 may be implanted via conventional surgical methods, or may be inserted using other endoscopic or laparoscopic techniques. A more complicated surgical procedure may be required for fixing the microstimulator in place.

The external surfaces of microstimulator SCU 160 may advantageously be composed of biocompatible materials. Capsule 152 may be made of, for instance, glass or ceramic to provide a hermetic package that will exclude water vapor but permit passage of electromagnetic fields used to transmit data and/or power. Electrodes 172 and 172' may be made of a noble or refractory metal, such as platinum, iridium, tantalum, titanium, niobium or their alloys, in order to avoid corrosion or electrolysis which could damage the surrounding tissues and the device.

In certain embodiments of the instant invention, microstimulator SCU 160 comprises two, leadless electrodes. However, either or both electrodes 172 and 172' may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of microstimulator SCU 160, while allowing most elements of the microstimulator to be located in a more surgically convenient site. This minimizes the distance traversed and the surgical planes crossed by the device and any lead(s). In most uses of this invention, the leads are no longer than about 150 mm.

As mentioned earlier, stimulation is provided in accordance with the teachings of the present invention by electrical stimulation and/or one or more stimulating drugs. The invention includes one or more system control units (SCUs). In the case of electrical stimulation only, SCUs include a microstimulator and/or an implantable pulse/signal generator (IPG), or the like. In the case of drug infusion only, an SCU comprises an implantable pump or the like. In cases requiring both electrical stimulation and drug infusion, more than one SCU may be used. Alternatively, when needed and/or desired, an SCU provides both electrical stimulation and one or more stimulating drugs.

Figure 5:
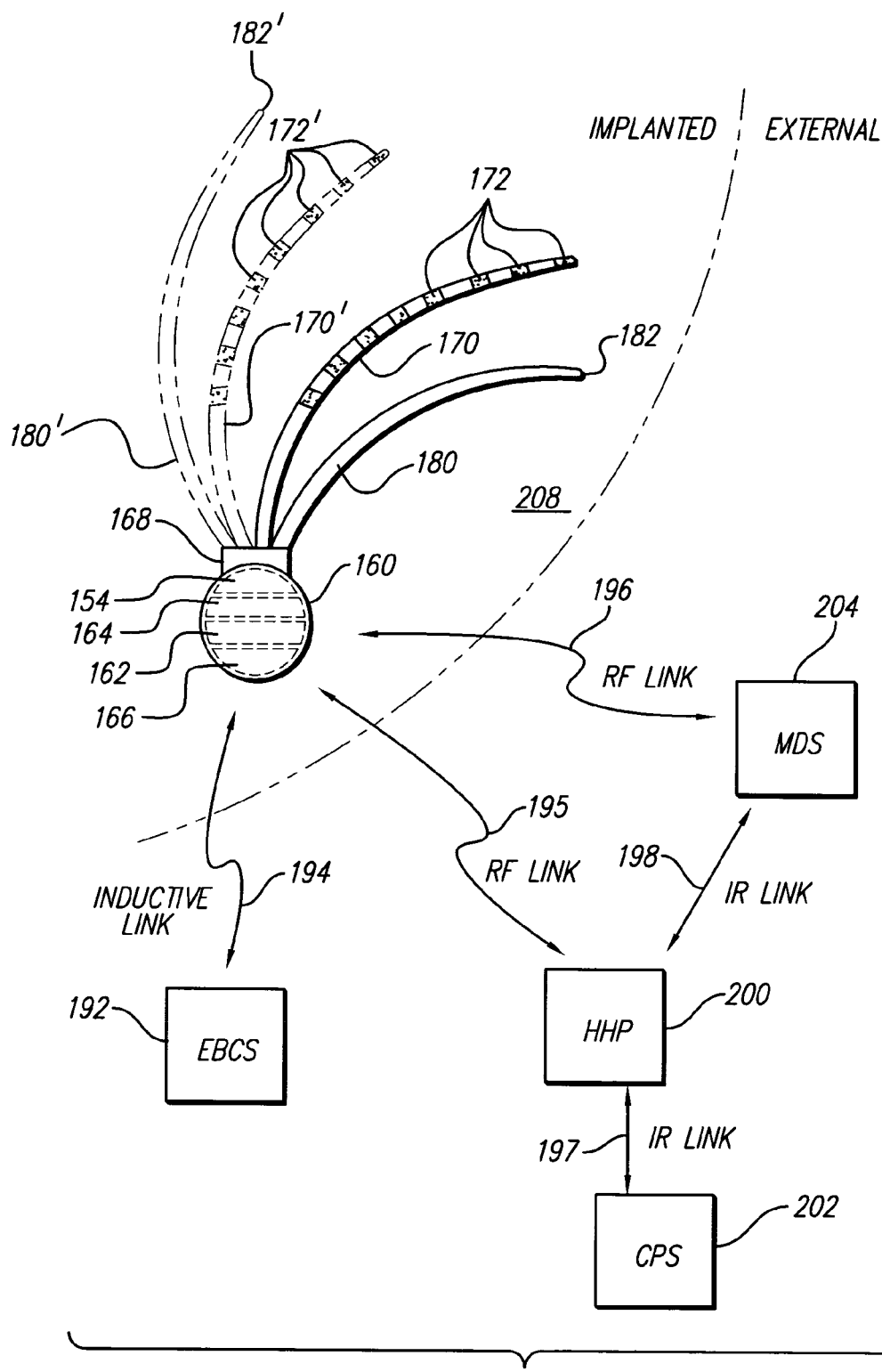
FIG. 5 depicts internal and external components of certain embodiments of the invention.

As depicted in FIG. 5, some embodiments of SCU 160 may be (but are not necessarily) implanted in a surgically-created shallow depression or opening, such as in the abdomen or above the buttock. In several embodiments, SCU 160 conforms to the profile of surrounding tissue(s) and/or bone(s), and is small and compact. This may minimize upward pressure applied to the skin, which pressure may result in skin erosion or infection. In various embodiments, SCU 160 has a diameter of about 75 mm, or only about 65 mm, or even less than about 55 mm. In these configurations, SCU thickness may be approximately 10-12 mm, or even less than about 10 mm.

As seen in the embodiments depicted in FIG. 5, one or more electrode leads 170 and/or catheters 180 attached to SCU 160 run subcutaneously, for instance, in a surgically-created shallow groove(s) or channel(s) or in a fascial plane (s). Recessed placement of the SCU and the lead(s) and/or catheter(s) may decrease the likelihood of erosion of overlying skin, and may minimize any cosmetic impact.

In embodiments such as in FIG. 5, electrode(s) 172 are carried on lead 170 having a proximal end coupled to SCU 160. The lead contains wires electrically connecting electrodes 172 to SCU 160. SCU 160 contains electrical components 154 that produce electrical stimulation pulses that travel through the wires of lead 170 and are delivered to electrodes 172, and thus to the tissue surrounding electrodes 172. To protect the electrical components inside SCU 160, some or all of the case of the SCU may be hermetically sealed. For additional protection against, e.g., impact, the case may be made of metal (e.g. titanium) or ceramic, which materials are also, advantageously, biocompatible. In addition, SCU 160 may be configured to be Magnetic Resonance Imaging (MRI) compatible.

In some alternatives, the electrical stimulation may be provided as described in International Patent Application Serial Number PCT/US00/20294 (the '294 application), filed Jul. 26, 2000, which application is incorporated herein by reference in its entirety. The '294 application is directed to a "Rechargeable Spinal Cord Stimulator System." In other alternatives, the electrical stimulation may be as provided in International Patent Application Serial Number PCT/US01/04417, filed Feb. 12, 2001, which application is also incorporated herein by reference in its entirety. The '417 application is directed to a "Deep Brain Stimulation System for the Treatment of Parkinson's Disease or Other Disorders".

In the case of treatment alternatively or additionally constituting drug infusion, SCU 160 may contain at least one pump 162 for storing and dispensing one or more drugs through infusion outlet(s) 182 and/or catheter(s) 180 into a predetermined site. When a catheter is used, it includes at least one infusion outlet 182, usually positioned at least at a distal end, while a proximal end of the catheter is connected to SCU 160.

According to some embodiments of the invention, such as described in the previously referenced PCT applications and as depicted in FIG. 5, at least one lead 170 is attached to SCU 160, via a suitable connector 168, if necessary. Each lead includes at least two electrodes 172, and may include as many as sixteen or more electrodes 172. Additional leads 170' and/or catheter(s) 180' may be attached to SCU 160. Hence, FIG. 5 shows (in phantom lines) a second catheter 180', and a second lead 170', having electrodes 172' thereon, also attached to SCU 160. Similarly, the SCUs 160 of FIGS. 4A, 4B, and 4C have outlets 182, 182' for infusing a stimulating drug(s) and electrodes 172, 172' for applying electrical stimulation.

Lead(s) 170 of certain embodiments of the present invention may be less than about 5 mm in diameter, or even less than about 1.5 mm in diameter. Electrodes 172, 172' on leads 170, 170' may be arranged as an array, for instance, as two or more collinear electrodes, or even as four or more collinear electrodes, or they may not be collinear. A tip electrode may also be supplied at the distal end of one or more leads. In some embodiments, SCU 160 is programmable to produce either monopolar electrical stimulation, e.g., using the SCU case as an indifferent electrode, or bipolar electrical stimulation, e.g., using one of the electrodes of the electrode array as an indifferent electrode. Some embodiments of SCU 160 have at least four channels and drive up to sixteen electrodes or more.

SCU 160 (which herein refers to IPGs, implantable pumps, IPG/pump combinations, microstimulators for drug and/or electrical stimulation, other alternative devices described herein, and the like) contains, when necessary and/or desired, electronic circuitry 154 for receiving data and/or power from outside the body by inductive, radio frequency (RF), or other electromagnetic coupling. In some embodiments, electronic circuitry 154 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

SCU 160 also includes, when necessary and/or desired, a programmable memory 164 for storing a set(s) of data, stimulation, and control parameters. Among other things, memory 164 may allow electrical and/or drug stimulation to be adjusted to settings that are safe and efficacious with minimal discomfort for each individual. Specific parameters may provide therapy for various types and degrees of severity of diabetes. For instance, some patients may respond favorably to intermittent stimulation, while others may require continuous treatment for relief. In some embodiments, electrical and drug stimulation parameters are controlled independently. In various embodiments, they are coupled, e.g., electrical stimulation is programmed to occur only during drug infusion.

In addition, parameters may be chosen to target specific tissues and to exclude others. For example, parameters may be chosen to increase neural activity in specific neural populations and to decrease neural activity in others. As another example, relatively low frequency neurostimulation (i.e., less than about 50-100 Hz) typically has an excitatory effect on surrounding neural tissue, leading to increased neural activity, whereas relatively high frequency neurostimulation (i.e., greater than about 50-100 Hz) may have an inhibitory effect, leading to decreased neural activity. Similarly, excitatory neurotransmitters (e.g., acetylcholine), agonists thereof, and agents that increase levels of an excitatory neurotransmitter(s) (e.g., edrophonium) generally have an excitatory effect on neural tissue, while inhibitory neurotransmitters (e.g., gamma-aminobutyric acid, a.k.a. GABA), agonists thereof, and agents that act to increase levels of an inhibitory neurotransmitter(s) generally have an inhibitory effect. However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g. atropine) and agents that decrease levels of excitatory neurotransmitters may inhibit neural activity.

Some embodiments of SCU 160 also include a power source and/or power storage device 166. Possible power options for a stimulation device of the present invention, described in more detail below, include but are not limited to an external power source coupled to the stimulation device, e.g., via an RF link, a self-contained power source utilizing any means of generation or storage of energy (e.g., a primary battery, a rechargeable battery such as a lithium ion battery, an electrolytic capacitor, or a super- or ultra-capacitor), and if the self-contained power source is replenishable or rechargeable, means of replenishing or recharging the power source (e.g., an RF link).

In embodiments such as shown in FIG. 5, SCU 160 includes a rechargeable battery as a power source/storage device 166. The battery is recharged, as required, from an external battery charging system (EBCS) 192, typically through an inductive link 194. In these embodiments, and as explained more fully in the earlier referenced PCT applications, SCU 160 includes a processor and other electronic circuitry 154 that allow it to generate stimulation pulses that are applied to a patient 208 through electrodes 172 and/or outlet(s) 182 in accordance with a program and stimulation parameters stored in programmable memory 164. Stimulation pulses of drugs include various types and/or rates of infusion, such as intermittent infusion, infusion at a constant rate, and bolus infusion.

According to certain embodiments of the invention, an SCU operates independently. According to various embodiments of the invention, an SCU operates in a coordinated manner with other SCU(s), other implanted device(s), or other device(s) external to the patient's body. For instance, an SCU may control or operate under the control of another implanted SCU(s), other implanted device(s), or other device(s) external to the patient's body. An SCU may communicate with other implanted SCUs, other implanted devices, and/or devices external to a patient's body via, e.g., an RF link, an ultrasonic link, or an optical link. Specifically, an SCU may communicate with an external remote control (e.g., patient and/or physician programmer) that is capable of sending commands and/or data to an SCU and that may also be capable of receiving commands and/or data from an SCU.

For example, some embodiments of SCU 160 of the present invention may be activated and deactivated, programmed and tested through a hand held programmer (HHP) 200 (which may also be referred to as a patient programmer and may be, but is not necessarily, hand held), a clinician programming system (CPS) 202 (which may also be hand held), and/or a manufacturing and diagnostic system (MDS) 204 (which may also be hand held). HHP 200 may be coupled to SCU 160 via an RF link 195. Similarly, MDS 204 may be coupled to SCU 160 via another RF link 196. In a like manner, CPS 202 may be coupled to HHP 200 via an infra-red link 197; and MDS 204 may be coupled to HHP 200 via another infra-red link 198. Other types of telecommunicative links, other than RF or infra-red may also be used for this purpose. Through these links, CPS 202, for example, may be coupled through HHP 200 to SCU 160 for programming or diagnostic purposes. MDS 204 may also be coupled to SCU 160, either directly through the RF link 196, or indirectly through IR link 198, HHP 200, and RF link 195.

Figure 6:
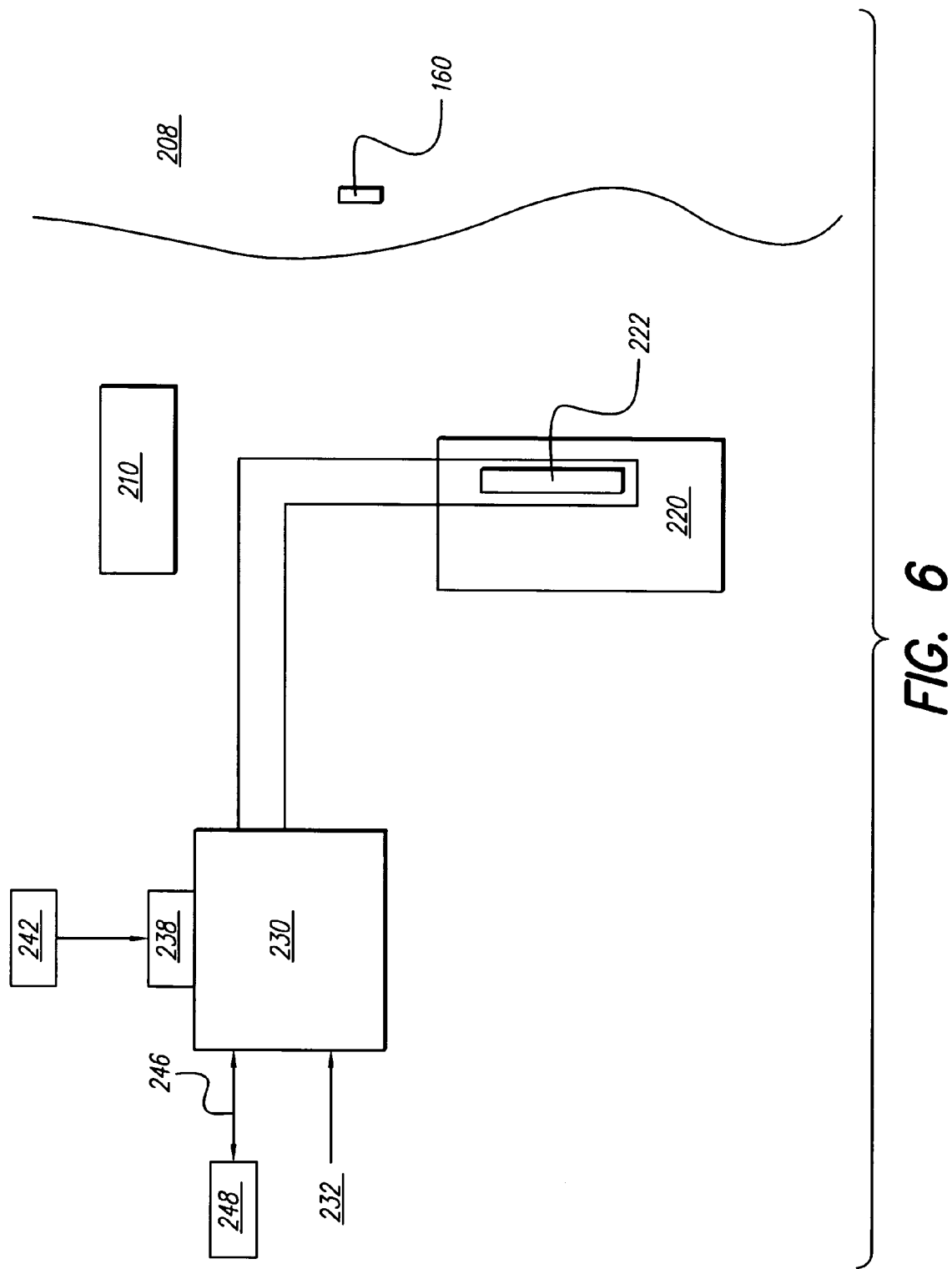
FIG. 6 illustrates external components of various embodiments of the invention.

In certain embodiments, using for example, a BION microstimulator(s) as described in the above referenced patents, and as illustrated in FIG. 6, the patient 208 switches SCU 160 on and off by use of controller 210, which may be hand held. Controller 210 operates to control SCU 160 by any of various means, including sensing the proximity of a permanent magnet located in controller 210, sensing RF transmissions from controller 210, or the like.

External components of various embodiments for programming and providing power to SCU 160 are also illustrated in FIG. 6. When it is required to communicate with SCU 160, patient 208 is positioned on or near external appliance 220, which appliance contains one or more inductive coils 222 or other means of communication (e.g., RF transmitter and receiver). External appliance 220 is connected to or is a part of external electronic circuitry appliance 230 which may receive power 232 from a conventional power source. External appliance 230 contains manual input means 238, e.g., a keypad, whereby the patient 208 or a caregiver 242 may request changes in electrical and/or drug stimulation parameters produced during the normal operation of SCU 160. In these embodiments, manual input means 238 includes various electro-mechanical switches and/or visual display devices that provide the patient and/or caregiver with information about the status and prior programming of SCU 160.

Alternatively or additionally, external electronic appliance 230 is provided with an electronic interface means 246 for interacting with other computing means 248, such as by a serial interface cable or infrared link to a personal computer or to a telephone modem or the like. Such interface means 246 may permit a clinician to monitor the status of the implant and prescribe new stimulation parameters from a remote location.

The external appliance(s) may be embedded in a cushion, pillow, mattress cover, or garment. Other possibilities exist, including a belt or other structure that may be affixed to the patient's body or clothing.

In order to help determine the strength and/or duration of electrical stimulation and/or the amount and/or type(s) of stimulating drug(s) required to produce the desired effect, in some embodiments, a patient's response to and/or need for treatment is sensed. For example, electrical activity of the brain (e.g., EEG), nerve activity (e.g., ENG), muscle activity (e.g., EMG), gastric distention, or other activity may be sensed. Additionally or alternatively, one or more neurotransmitter levels and/or their associated breakdown product levels, hormone levels, cytokine levels, or other substances, such as ketone, glucose, electrolyte, enzyme, and/or medication levels and/or changes in these or other substances in the blood plasma or local interstitial fluid, may be sensed.

For example, when electrodes of SCU 160 are implanted adjacent to at least one of the celiac ganglia 140, a stimulating electrode of SCU 160, or other sensing means, may be used to sense changes in insulin level resulting from the electrical and/or drug stimulation applied to the at least one celiac ganglion 140. (As used herein, "adjacent" or "near" means as close as reasonably possible to targeted tissue, including touching or even being positioned within the tissue, but in general, may be as far as about 150 mm from the target tissue.)

Alternatively, an "SCU" dedicated to sensory processes communicates with an SCU that provides the stimulation pulses. The implant circuitry 154 may, if necessary, amplify and transmit these sensed signals, which may be digital or analog. Other methods of determining the required electrical and/or drug stimulation include measuring impedance, acidity/alkalinity (via a pH sensor), body mass, and other methods mentioned herein, and others that will be evident to those of skill in the art upon review of the present disclosure. The sensed information may be used to control stimulation parameters in a closed-loop manner.

For instance, in several embodiments of the present invention, a first and second "SCU" are provided. The second "SCU" periodically (e.g. once per minute) records glucose level (or the level of insulin or of some other substance, or an amount of electrical activity, etc.), which it transmits to the first SCU. The first SCU uses the sensed information to adjust electrical and/or drug stimulation parameters according to an algorithm programmed, e.g., by a physician. For example, the amplitude of electrical stimulation may be increased in response to decreased insulin levels. In some alternatives, one SCU performs both the sensing and stimulating functions, as discussed in more detail presently.

While an SCU 160 may also incorporate means of sensing diabetes or symptoms or other prognostic or diagnostic indicators of diabetes, e.g., via levels of a neurotransmitter or hormone, it may alternatively or additionally be desirable to use a separate or specialized implantable device to record and telemeter physiological conditions/responses in order to adjust electrical stimulation and/or drug infusion parameters. This information may be transmitted to an external device, such as external appliance 220, or may be transmitted directly to implanted SCU(s) 160. However, in some cases, it may not be necessary or desired to include a sensing function or device, in which case stimulation parameters are determined and refined, for instance, by patient feedback, or the like.

Thus, it is seen that in accordance with the present invention, one or more external appliances may be provided to interact with SCU 160, and may be used to accomplish, potentially among other things, one or more of the following functions:

Function 1: If necessary, transmit electrical power from the external electronic appliance 230 via appliance 220 to SCU 160 in order to power the device and/or recharge the power source/storage device 166. External electronic appliance 230 may include an automatic algorithm that adjusts electrical and/or drug stimulation parameters automatically whenever the SCU(s) 160 is/are recharged.

Function 2: Transmit data from the external appliance 230 via the external appliance 220 to SCU 160 in order to change the parameters of electrical and/or drug stimulation produced by SCU 160.

Function 3: Transmit sensed data indicating a need for treatment or in response to stimulation from SCU 160 (e.g., glucose level, electrical activity of the brain, nerve activity, muscle activity, neurotransmitter levels, levels of neurotransmitter breakdown products, impedance, acidity/alkalinity, medication levels, hormone levels, or other activity) to external appliance 230 via external appliance 220.

Function 4: Transmit data indicating state of the SCU 160 (e.g., battery level, drug level, stimulation parameters, etc.) to external appliance 230 via external appliance 220.

By way of example, a treatment modality for diabetes may be carried out according to the following sequence of procedures:

1. An SCU 160 is implanted so that its electrodes 172 and/or infusion outlet 182 are located in or near one or both celiac ganglia 140. If necessary or desired, electrodes 172' and/or infusion outlet(s) 182' may additionally or alternatively be located in or adjacent to other autonomic ganglia and/or nerves, such as branches of the vagus or splanchnic nerves, and/or may be located adjacent islets of Langerhans or pancreatic alpha, beta, and/or delta cells.

2. Using Function 2 described above (i.e., transmitting data) of external electronic appliance 230 and external appliance 220, SCU 160 is commanded to produce a series of inhibitory electrical stimulation pulses, possibly with gradually increasing amplitude, and possibly while infusing gradually increasing amounts of a parasympathetic agonist, e.g., methacholine, into naturally occurring and/or transplanted pancreatic beta cells.

3. After each stimulation pulse, or at some other predefined interval, any change in glucose and/or insulin level resulting from the electrical and/or drug stimulation is sensed, for instance, by one or more electrodes 172 and/or 172'. These responses are converted to data and telemetered out to external electronic appliance 230 via Function 3.

4. From the response data received at external appliance 230 from SCU 160, the stimulus threshold for obtaining a response is determined and is used by a clinician 242 acting directly 238 or by other computing means 248 to transmit the desired electrical and/or drug stimulation parameters to SCU 160 in accordance with Function 2.

5. When patient 208 desires to invoke electrical stimulation and/or drug infusion, patient 208 employs controller 210 to set SCU 160 in a state where it delivers a prescribed stimulation pattern from a predetermined range of allowable stimulation patterns.

6. To cease electrical and/or drug stimulation, patient 208 employs controller 210 to turn off SCU 160.

7. Periodically, the patient or caregiver recharges the power source/storage device 166 of SCU 160, if necessary, in accordance with Function 1 described above (i.e., transmit electrical power).

For the treatment of any of the various types and degrees of severity of diabetes, it may be desirable to modify or adjust the algorithmic functions performed by the implanted and/or external components, as well as the surgical approaches, in ways that would be obvious to skilled practitioners of these arts. For example, in some situations, it may be desirable to employ more than one SCU 160, each of which could be separately controlled by means of a digital address. Multiple channels and/or multiple patterns of electrical and/or drug stimulation might thereby be programmed by the clinician and controlled by the patient in order to deal with complex or multiple diseases, symptoms, or dysfunctions.

In some embodiments discussed earlier, SCU 160, or a group of two or more SCUs, is controlled via closed-loop operation. A need for and/or response to stimulation is sensed via SCU 160, or by an additional SCU (which may or may not be dedicated to the sensing function), or by another implanted or external device.

If necessary, the sensed information is transmitted to SCU 160. In some embodiments, the parameters used by SCU 160 are automatically adjusted based on the sensed information. Thus, the electrical and/or drug stimulation parameters are adjusted in a closed-loop manner to provide stimulation tailored to the need for and/or response to the electrical and/or drug stimulation.

Figure 7:
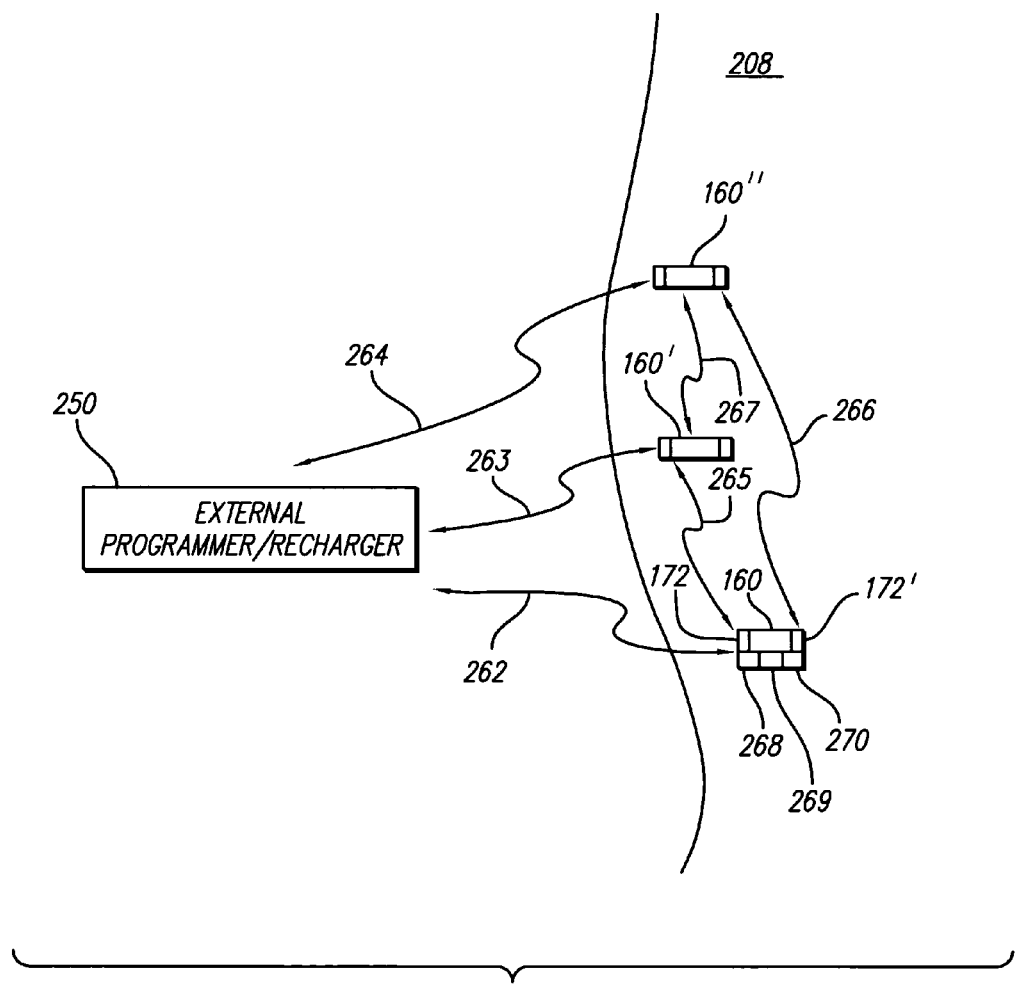
FIG. 7 depicts a system of implantable devices that communicate with each other and/or with external control/programming devices.

For instance, as shown in the example of FIG. 7, a first SCU 160, implanted beneath the skin of the patient 208, provides a first medication or substance; a second SCU 160' provides a second medication or substance; and a third SCU 160" provides electrical stimulation via electrodes 172 and 172'. As mentioned earlier, the implanted devices may operate independently or may operate in a coordinated manner with other similar implanted devices, other implanted devices, or other devices external to the patient's body, as shown by the control lines 262, 263 and 264 in FIG. 7. That is, in accordance with certain embodiments of the invention, the external controller 250 controls the operation of each of the implanted devices 160, 160' and 160". According to various embodiments of the invention, an implanted device, e.g. SCU 160, may control or operate under the control of another implanted device(s), e.g. SCU 160' and/or SCU 160". That is, a device made in accordance with the invention may communicate with other implanted stimulators, other implanted devices, and/or devices external to a patient's body, e.g., via an RF link, an ultrasonic link, an optical link, or the like. Specifically, as illustrated in FIG. 7, SCU 160, 160', and/or 160", made in accordance with the invention, may communicate with an external remote control (e.g., patient and/or physician programmer 250) that is capable of sending commands and/or data to implanted devices and that may also be capable of receiving commands and/or data from implanted devices.

A drug infusion stimulator made in accordance with the invention may incorporate communication means for communicating with one or more external or site-specific drug delivery devices, and, further, may have the control flexibility to synchronize and control the duration of drug delivery. The associated drug delivery device typically provides a feedback signal that lets the control device know it has received and understood commands. The communication signal between the implanted stimulator and the drug delivery device may be encoded to prevent the accidental or inadvertent delivery of drugs by other signals.

An SCU made in accordance with the invention thus incorporates, in some embodiments, first sensing means 268 for sensing therapeutic effects, clinical variables, or other indicators of the state of the patient, such as EEG, ENG, EMG, gastric distention, impedance, pH, body mass, or the like. The stimulator additionally or alternatively incorporates second means 269 for sensing neurotransmitter levels and/or their associated breakdown product levels, medication levels and/ or other drug levels, insulin, hormone, glucose, ketone, electrolytes, enzyme, and/or cytokine levels and/or changes in these or other substances in the blood plasma or local interstitial fluid. The stimulator additionally or alternatively incorporates third means 270 for sensing electrical current levels and/or waveforms supplied by another source of electrical energy. Sensed information may be used to control infusion and/or electrical parameters in a closed loop manner, as shown by control lines 266, 267, and 265. Thus, sensing means may be incorporated into a device that also includes electrical and/or drug stimulation, or the sensing means (that may or may not have stimulating means) may communicate the sensed information to another device(s) with stimulating means.

According to certain embodiments of the invention, the electrodes of an SCU are implanted adjacent to pancreatic beta cells in order to effect modulation of insulin secretion for therapy in diabetic patients. These may be beta cells of the patient or may be transplanted beta cells. An SCU effects depolarization of these beta cells through the application of an appropriate electrical pulse. It is known in the art how to apply an appropriate electrical pulse to depolarize, or to hyperpolarize, a cell. As described above, voltage-regulated calcium ion (Ca++) channels will open in response to cellular depolarization, allowing an influx of Ca++. Elevated intracellular Ca++ leads to activation of protein kinases and ultimately to fusion of insulin-containing secretory granules with the beta cell membrane, thus leading to exocytosis of insulin into the systemic circulation.

Additionally or alternatively, an SCU may be implanted with electrodes adjacent to alpha and/or delta cells. By applying an electrical pulse to hyperpolarize alpha cells, the secretion of glucagon by alpha cells is inhibited. By applying an electrical pulse to hyperpolarize delta cells, the secretion of somatostatin by delta cells is inhibited. Inhibition of glucagon and/or somatostatin prevents their inhibition of insulin secretion.

An SCU may also/instead apply an electrical pulse to hyperpolarize beta cells. This effectively inhibits the secretion of insulin, which is therapeutic during periods of hypoglycemia. Additionally or alternatively, an SCU may apply an electrical pulse to depolarize alpha cells, which increases the secretion of glucagon, and/or delta cells, which increases the secretion of somatostatin. The secretion of insulin is inhibited by the presence of glucagon and/or somatostatin. Again, this is therapeutic during periods of hypoglycemia.

Selective stimulation of beta, alpha, and delta cells is possible due to segregation of cells in the pancreatic islets. More than one SCU 160 or multiple electrodes 172, 172' may be implanted to achieve hyperpolarization (or depolarization) of a larger number of specific islet cells.

According to certain embodiments of the invention, stimulation may be applied to sympathetic and/or parasympathetic nerves and/or ganglia that innervate the pancreatic islets. As mentioned earlier, different parameters of electrical stimulation may result in significantly different responses from autonomic nerve fibers, and parameters may be chosen to target specific neural populations and to exclude others. Relatively low frequency neurostimulation (i.e., less than about 50-100 Hz) tends to have an excitatory effect on neural tissue, whereas relatively high frequency neurostimulation (i.e., greater than about 50-100 Hz) tends to have an inhibitory effect. Thus, electrical stimulation may be used to excite or to inhibit neural activity.

In some embodiments of the present invention, stimulation increases excitement of parasympathetic input to the pancreatic beta cells, for instance, the posterior gastric, anterior gastric, celiac, and/or hepatic branches of the vagus nerve, thereby increasing insulin secretion and treating hyperglycemia in a diabetic patient. Additionally, as described above, the response of beta cells, and of abdominal and thoracic organs, to parasympathetic activity depends in part on the frequency of electrical stimulation. Stimulation may be applied at frequencies that maximize pancreatic islet cell response, while limiting the stimulation of the heart, stomach, and other organs of the gastrointestinal tract. For example, electrical stimulation of parasympathetic targets may be applied at approximately 3-12 Hz, or at approximately 3-8 Hz, or at approximately 3-5 Hz.

In certain embodiments of the present invention, stimulation decreases excitement of the sympathetic input to the pancreatic beta cells. For instance, inhibitory stimulation (i.e., greater than about 50-100 Hz) may be applied to one or more of the right and left, greater, lesser, and least splanchnic nerves 130 and 132 and/or to one or more of the sympathetic ganglia innervating the pancreas (i.e., celiac ganglia 140, aorticorenal ganglia 142, super mesenteric ganglion 144, inferior mesenteric ganglion 146, phrenic ganglion 148, and ganglia of the paraspinal sympathetic trunks 124 and 126). This sympathetic inhibition may increase insulin secretion, thus treating hyperglycemia in a diabetic patient. In addition, this sympathetic inhibition is likely to inhibit secretion of glucagon, thereby preventing glucagon from inhibiting insulin secretion and insulin effects on target tissues.

During periods of hypoglycemia, parasympathetic input may be inhibited and/or sympathetic input may be activated in order to decrease insulin secretion and increase glucagon secretion. In this case, various embodiments of the invention provide relatively high-frequency stimulation (i.e., greater than about 50-100 Hz) to parasympathetic nerves innervating the pancreas, such as to the posterior gastric, anterior gastric, celiac, and hepatic branches of the vagus nerve, thereby decreasing insulin secretion and/or increasing glucagon secretion and treating a patient with hypoglycemia.

Additionally or alternatively, relatively low-frequency stimulation (i.e. less than about 50-100 Hz) may be applied to sympathetic nerves and/or ganglia innervating the pancreas to inhibit insulin secretion. This excitatory stimulation may be applied to one or more of the right and left, greater, lesser, and least splanchnic nerves 130 and 132 and/or to one or more sympathetic ganglia innervating the pancreas (i.e., celiac ganglia 140, aorticorenal ganglia 142, super mesenteric ganglion 144, inferior mesenteric ganglion 146, phrenic ganglion 148, and ganglia of the paraspinal sympathetic trunks 124 and 126). In addition, this excitatory sympathetic stimulation is likely to activate secretion of glucagon, thereby further inhibiting insulin secretion.

In addition or instead of electrical stimulation, one or more SCUs may deliver excitatory or inhibitory substances to pancreatic islet cells. As described earlier, one or more discharge portion(s) 182/182', possibly positioned on one or more catheters 180/180', may be surgically implanted at one or more pancreatic islets, pancreatic beta cells graft(s), parasympathetic nerves, and/or sympathetic nerves and/or ganglia.

In some embodiments, to treat hyperglycemia, an SCU(s) may release substances into an islet(s) and/or graft(s) that increase insulin secretion, including glucose, K+, Ca++, arginine, lysine, acetylcholine, cholinergic agonist(s), beta-adrenergic agonist(s), alpha-adrenergic antagonist(s), glucagon, glucagon-like peptide 1, gastric inhibitory peptide (GIP), secretin, cholecystokinin (CCK), and beta-3-agonist(s). Additionally or alternatively, an SCU(s) may release substances into an islet(s) and/or graft(s) that inhibit glucagon secretion, including alpha-adrenergic antagonists, glucose, insulin, and somatostatin.

In several embodiments, hyperglycemia may be treated by releasing substances in or near parasympathetic synapses to excite parasympathetic activity. These excitatory substances include at least one of a parasympathetic neurotransmitter agonist(s) (e.g., acetylcholine), a medication that increases the level of an excitatory neurotransmitter (e.g., edrophnium), an excitatory hormone agonists(s), an inhibitory neurotransmitter antagonist(s), an inhibitory hormone antagonist(s), and/or the like. One or more of these substances may be released in or near one or more of the parasympathetic ganglia and/or sites of postganglionic parasympathetic synapses.

In certain embodiments, hyperglycemia may be treated by releasing substances in or near sympathetic synapses to inhibit sympathetic activity. These inhibitory substances include at least one of a sympathetic neurotransmitter antagonist(s) (e.g., mecamylamine acting on a sympathetic ganglion/ganglia, and/or phentolamine and/or propranolol acting on a postganglionic synapse(s)), a medication that decreases the level of a sympathetic neurotransmitter (e.g., metyrosine), an inhibitory hormone agonist(s), an excitatory hormone antagonist(s), and/or the like. Some of these substances are known as adrenoceptor antagonist medications and/or autonomic ganglion-blocking medications. One or more of the above substances may be released in or near one or more of the celiac ganglia 140, aorticorenal ganglia 142, super mesenteric ganglion 144, inferior mesenteric ganglion 146, phrenic ganglion 148, ganglia of the paraspinal sympathetic trunks 124 and 126, and/or at sites of postganglionic sympathetic synapses.

In various embodiments, to treat hypoglycemia, an SCU(s) may release substances into an islet(s) and/or graft(s) that inhibit insulin secretion, including alpha-adrenergic agonists, cholinergic antagonists, beta-adrenergic antagonists, somatostatin, galanin, pancreastatin, and leptin. Additionally or alternatively, an SCU(s) may release substances that promote glucagon secretion, including alpha-adrenergic agonists, arginine, and alanine.

In some embodiments, hypoglycemia may be treated by releasing substances in or near parasympathetic synapses to inhibit parasympathetic activity. These inhibitory substances include at least one of an inhibitory neurotransmitter agonist (s), a medication that increases the level of an inhibitory neurotransmitter, an inhibitory hormone agonist(s), an parasympathetic neurotransmitter antagonist(s) (e.g., atropine acting on a postganglionic synapses(s) and/or mecamylamine acting on a parasympathetic ganglion/ganglia), an excitatory hormone antagonist(s), and/or the like. Some of these substances are known as cholinoceptor-blocking medications and/or autonomic ganglion-blocking drugs. One or more of the above substances may be released in or near one or more of the parasympathetic ganglia and/or sites of postganglionic parasympathetic synapses.

In several embodiments, hypoglycemia may be treated by releasing substances in or near sympathetic synapses to excite sympathetic activity. These substances include at least one of an sympathetic neurotransmitter agonist(s) (e.g., norepinephrine), a medication that increases the level of an excitatory neurotransmitter, an excitatory hormone agonists(s) (e.g., epinephrine), an inhibitory neurotransmitter antagonist(s), an inhibitory hormone antagonist(s), and/or the like. Some of these substances are known as adrenoceptor-activating and/or sympathomimetic medications. One or more of these substances may be released in or near one or more of the celiac ganglia 140, aorticorenal ganglia 142, super mesenteric ganglion 144, inferior mesenteric ganglion 146, phrenic ganglion 148, ganglia of the paraspinal sympathetic trunks 124 and 126, and/or at sites of postganglionic sympathetic synapses.

In certain embodiments, sensing means described earlier may be used to orchestrate first the activation of SCU(s) targeting one or more autonomic and/or pancreatic tissues, and then, when appropriate, the SCU(s) targeting another area(s) and/or by a different means. Alternatively, this orchestration may be programmed, and not based on a sensed condition.

Additional potential (but not necessary) uses of the present invention include, but are not limited to, application to diabetes prevention, as mentioned earlier.

While the invention herein disclosed has been described by means of specific embodiments and applications thereof, numerous modifications and variations could be made thereto by those skilled in the art without departing from the scope of the invention set forth in the claims.

What is claimed is:

1. A system for modulating pancreatic endocrine secretions of a patient, comprising:
   an implantable control unit adapted to be implanted in the body of a patient, wherein the control unit includes means for controlling the delivery of at least one stimulus to at least one type of pancreatic cell affecting pancreatic endocrine secretions; and
   means for applying the at least one stimulus to the at least one type of pancreatic cell in order to hyperpolarize the at least one type of pancreatic cell and thereby modulate at least one pancreatic endocrine secretion;
   wherein the at least one type of pancreatic cell is selected from the group comprising: an alpha cell wherein the hyperpolarization inhibits secretion of glucagon, and a delta cell wherein the hyperpolarization inhibits secretion of somatostatin.

2. A system for modulating pancreatic endocrine secretions of a patient, comprising:
   an implantable control unit adapted to be implanted in the body of a patient, wherein the control unit includes means for controlling the delivery of at least one stimulus to at least one type of pancreatic cell affecting pancreatic endocrine secretions; and
   means for applying the at least one stimulus to the at least one type of pancreatic cell in order to depolarize the at least one type of pancreatic cell to thereby increase secretion of a substance that inhibits insulin secretion;
   wherein the at least one type of pancreatic cell is selected from the group comprising: an alpha cell wherein the depolarization increases secretion of glucagon, and a delta cell wherein the depolarization increases secretion of somatostatin.

3. A system of modulating pancreatic endocrine secretions of a patient, comprising:
   an implantable control unit adapted to be implanted in the body of a patient, wherein the control unit includes means for controlling the delivery of stimulation to at least one parasympathetic tissue innervating the pancreas; and
   means for applying the stimulation to the at least one parasympathetic tissue in order to minimize stimulation of gastrointestinal structures and the heart while maximizing stimulation of pancreatic beta cells, whereby insulin secretion is increased;
   wherein the system control unit is connected to at least two implantable electrodes, and wherein the means for applying the stimulation comprises means for applying electrical stimulation via the at least two implantable electrodes at a frequency that ranges between about 3 to 12 Hz.

4. The system of claim 3 wherein the means for applying the stimulation to the at least one parasympathetic tissue comprises means for applying the stimulation to at least one of the posterior gastric, anterior gastric, celiac, and hepatic branches of the vagus nerve.

5. The system of claim 3 wherein the system control unit includes means for providing drug stimulation and wherein the means for applying the stimulation comprises means for providing at least one of a cholinoceptor-blocking medication and an autonomic ganglion-blocking medication to the parasympathetic tissue.

6. The system of claim 3 further comprising means for sensing a condition and means for using the sensed condition to automatically determine the stimulation to be applied.

7. A system of modulating pancreatic endocrine secretions of a patient, comprising:
an implantable control unit adapted to be implanted in the body of a patient, wherein the control unit includes means for controlling the delivery of stimulation to at least one parasympathetic tissue innervating the pancreas; and
means for applying the stimulation to the at least one parasympathetic tissue in order to minimize stimulation of gastrointestinal structures and the heart while maximizing stimulation of pancreatic beta cells, whereby insulin secretion is decreased; wherein the system control unit is connected to at least two implantable electrodes, and wherein the means for applying the stimulation comprises means for applying electrical stimulation via the at least two implantable electrodes at a frequency that is greater than about 50 Hz.

8. The system of claim 7 wherein the means for applying the stimulation to the at least one parasympathetic tissue comprises means for applying the stimulation to at least one of the posterior gastric, anterior gastric, celiac, and hepatic branches of the vagus nerve.

9. The system of claim 7 wherein the system control unit includes means for providing drug stimulation and wherein the means for applying the stimulation comprises means for providing at least one of a cholinoceptor-blocking medication and an autonomic ganglion-blocking medication to the parasympathetic tissue.

10. The system of claim 7 further comprising means for sensing a condition and means for using the sensed condition to automatically determine the stimulation to be applied.

11. A system of modulating pancreatic endocrine secretions of a patient, comprising:
an implantable system control unit adapted to be implanted in the body of a patient, wherein the system control unit includes means for delivering stimulation to at least one sympathetic tissue innervating the pancreas; and
means for controlling the stimulation delivered to the at least one sympathetic tissue in order to modulate at least one pancreatic endocrine secretion;
wherein the at least one sympathetic tissue to which the stimulation is delivered is selected from the group comprising: the ganglia of the paraspinal sympathetic trunks, celiac ganglia, aorticorenal ganglia, super mesenteric ganglion, inferior mesenteric ganglion, phrenic ganglion, left greater splanchnic nerve, left lesser splanchnic nerve, left least splanchnic nerve, right greater splanchnic nerve, right lesser splanchnic nerve, and right least splanchnic nerve;
wherein the stimulation delivered to the at least one sympathetic tissue is adapted to inhibit sympathetic input to the pancreas, whereby glucagon secretion is reduced; and
wherein the means for delivering stimulation includes at least two implantable electrodes, and wherein the means for controlling the stimulation comprises means for applying electrical stimulation to the at least two implantable electrodes at a frequency of greater than about 50 Hz.

12. The system of claim 11 further comprising means for sensing a condition and means for using the sensed condition to automatically determine the stimulation to be applied.

13. The system of claim 11 wherein the means for delivering stimulation comprises means for delivering drug stimulation, and wherein the means for controlling the stimulation comprises means for delivering an adrenoceptor antagonist medication or an autonomic ganglion-blocking medication to the sympathetic tissue.

14. A system of modulating pancreatic endocrine secretions of a patient, comprising:
an implantable system control unit adapted to be implanted in the body of a patient, wherein the system control unit includes means for delivering stimulation to at least one sympathetic tissue innervating the pancreas; and
means for controlling the stimulation delivered to the at least one sympathetic tissue in order to modulate at least one pancreatic endocrine secretion;
wherein the at least one sympathetic tissue to which the stimulation is delivered is selected from the group comprising: the ganglia of the paraspinal sympathetic trunks, celiac ganglia, aorticorenal ganglia, super mesenteric ganglion, inferior mesenteric ganglion, phrenic ganglion, left greater splanchnic nerve, left lesser splanchnic nerve, left least splanchnic nerve, right greater splanchnic nerve, right lesser splanchnic nerve, and right least splanchnic nerve;
wherein the means for controlling the stimulation is adapted to excite sympathetic input to the pancreas, whereby glucagon secretion is increased; and
wherein the implantable control unit is connected to at least two implantable electrodes, and wherein the means for delivering stimulation comprises means for delivering electrical stimulation via the at least two electrodes and wherein the means for controlling the stimulation comprises means for controlling the frequency of the electrical stimulation to be less than about 100 Hz.

15. The system of claim 14 wherein the means for delivering stimulation comprises means for delivering an adrenoceptor-activating medication or a sympathomimetic medication to the sympathetic tissue.

16. The system of claim 14 further comprising means for sensing a condition and means for using the sensed condition to automatically determine the stimulation to be applied.

* * * * *